(12) United States Patent
Gregerson et al.

(10) Patent No.: US 12,167,940 B2
(45) Date of Patent: Dec. 17, 2024

(54) METHODS AND SYSTEMS FOR DISPLAY OF PATIENT DATA IN COMPUTER-ASSISTED SURGERY

(71) Applicant: Mobius Imaging, LLC, Shirley, MA (US)

(72) Inventors: Eugene A. Gregerson, Bolton, MA (US); Scott Coppen, Amesbury, MA (US); Todd Furlong, Goffstown, NH (US); Edward Daley, Maynard, MA (US); Russell Stanton, Lunenberg, MA (US); Adeline Harris, Grass Valley, CA (US); Paul Sebring, Townsend, MA (US)

(73) Assignee: Mobius Imaging, LLC, Shirley, MA (US)

( * ) Notice: Subject to any disclaimer, the term of this patent is extended or adjusted under 35 U.S.C. 154(b) by 0 days.

(21) Appl. No.: 18/348,130

(22) Filed: Jul. 6, 2023

(65) Prior Publication Data
US 2023/0355347 A1   Nov. 9, 2023

Related U.S. Application Data

(63) Continuation of application No. 17/410,024, filed on Aug. 24, 2021, now Pat. No. 11,737,850, which is a
(Continued)

(51) Int. Cl.
*A61B 90/00* (2016.01)
*A61B 5/00* (2006.01)
(Continued)

(52) U.S. Cl.
CPC .............. *A61B 90/37* (2016.02); *A61B 5/055* (2013.01); *A61B 5/1127* (2013.01); *A61B 6/032* (2013.01);
(Continued)

(58) Field of Classification Search
None
See application file for complete search history.

(56) References Cited

U.S. PATENT DOCUMENTS 5,823,958 A   10/1998   Truppe
6,314,310 B1  11/2001   Ben-Haim et al.
(Continued)

FOREIGN PATENT DOCUMENTS

DE   102004054867 A1   5/2006
EP        2765946 B1   8/2015
(Continued)

OTHER PUBLICATIONS

International Preliminary Report on Patentability for PCT/US2017/050733, dated Mar. 21, 2019.
(Continued)

*Primary Examiner* — Ryan M Gray
(74) *Attorney, Agent, or Firm* — Howard & Howard Attorneys PLLC

(57) ABSTRACT

Methods and systems for performing computer-assisted image-guided surgery, including robotically-assisted surgery. A method of displaying image data includes displaying image data of a patient on a handheld display device, tracking the handheld display device using a motion tracking system, and modifying the image data displayed in response to changes in the position and orientation of the handheld display device. Further embodiments include a sterile case for a handheld display device, display devices on a robotic arm, and methods and systems for performing image-guided surgery using multiple reference marker devices fixed to a patient.

20 Claims, 17 Drawing Sheets

Related U.S. Application Data continuation of application No. 16/839,829, filed on Apr. 3, 2020, now Pat. No. 11,141,237, which is a continuation of application No. 15/701,063, filed on Sep. 11, 2017, now Pat. No. 10,653,495.

(60) Provisional application No. 62/385,552, filed on Sep. 9, 2016.

(51) Int. Cl.
| | |
|---|---|
| *A61B 5/055* | (2006.01) |
| *A61B 5/11* | (2006.01) |
| *A61B 6/03* | (2006.01) |
| *A61B 6/46* | (2024.01) |
| *A61B 34/10* | (2016.01) |
| *A61B 34/20* | (2016.01) |
| *A61B 34/30* | (2016.01) |
| *A61B 34/35* | (2016.01) |
| *A61B 90/50* | (2016.01) |
| *G06F 3/04883* | (2022.01) |
| *G06F 3/14* | (2006.01) |
| *G06T 7/246* | (2017.01) |
| *G06T 7/73* | (2017.01) |
| *G06T 15/08* | (2011.01) |
| *G06T 15/20* | (2011.01) |
| *G06T 19/00* | (2011.01) |

(52) U.S. Cl.
CPC .............. *A61B 6/461* (2013.01); *A61B 34/20* (2016.02); *A61B 34/30* (2016.02); *A61B 34/35* (2016.02); *A61B 90/00* (2016.02); *A61B 90/361* (2016.02); *A61B 90/50* (2016.02); *G06T 7/248* (2017.01); *G06T 7/74* (2017.01); *G06T 15/08* (2013.01); *G06T 15/20* (2013.01); *G06T 19/006* (2013.01); *A61B 5/0035* (2013.01); *A61B 5/7425* (2013.01); *A61B 6/463* (2013.01); *A61B 2034/105* (2016.02); *A61B 2034/2048* (2016.02); *A61B 2034/2057* (2016.02); *A61B 2034/2059* (2016.02); *A61B 2034/2065* (2016.02); *A61B 2034/2072* (2016.02); *A61B 2090/365* (2016.02); *A61B 2090/367* (2016.02); *A61B 2090/372* (2016.02); *A61B 2090/373* (2016.02); *A61B 2090/374* (2016.02); *A61B 2090/376* (2016.02); *A61B 2090/3762* (2016.02); *A61B 2090/378* (2016.02); *A61B 2090/3983* (2016.02); *A61B 2560/0223* (2013.01); *G06F 3/04883* (2013.01); *G06F 3/1446* (2013.01); *G06T 2207/30012* (2013.01)

(56) References Cited

U.S. PATENT DOCUMENTS

| | | | |
|---|---|---|---|
| 7,203,277 | B2 | 4/2007 | Birkenbach et al. |
| 7,535,411 | B2 | 5/2009 | Falco |
| 8,118,488 | B2 | 2/2012 | Gregerson |
| 8,126,535 | B2 | 2/2012 | Maier et al. |
| 8,682,413 | B2 | 3/2014 | Lloyd |
| 8,734,432 | B2 | 5/2014 | Tuma et al. |
| 8,998,797 | B2 | 4/2015 | Omori |
| 9,008,757 | B2 | 4/2015 | Wu |
| 9,283,048 | B2 | 3/2016 | Kostrzewski et al. |
| 9,345,441 | B2 | 5/2016 | Wendler |
| 9,436,993 | B1 | 9/2016 | Stolka |
| 9,498,132 | B2 | 11/2016 | Maier-Hein et al. |
| 9,538,962 | B1 | 1/2017 | Hannaford |
| 9,675,319 | B1 | 6/2017 | Razzaque |
| 9,949,798 | B2 | 4/2018 | Weir |
| 10,080,615 | B2 | 9/2018 | Bartelme et al. |
| 10,290,157 | B2 | 5/2019 | Nijlunsing |
| 10,653,495 | B2 | 5/2020 | Gregerson et al. |
| 11,141,237 | B2 | 10/2021 | Gregersen et al. |
| 2001/0037064 | A1 | 11/2001 | Shahidi |
| 2004/0105068 | A1 | 6/2004 | Wiedner |
| 2004/0105086 | A1 | 6/2004 | Leitner et al. |
| 2004/0263535 | A1 | 12/2004 | Birkenbach et al. |
| 2006/0173290 | A1 | 8/2006 | Lavallee |
| 2007/0236514 | A1 | 10/2007 | Agusanto et al. |
| 2008/0004603 | A1 | 1/2008 | Larkin et al. |
| 2008/0147089 | A1 | 6/2008 | Loh et al. |
| 2009/0177081 | A1 | 7/2009 | Joskowicz et al. |
| 2009/0306499 | A1 | 12/2009 | Van Vorhis et al. |
| 2010/0100081 | A1 | 4/2010 | Tuma et al. |
| 2010/0168562 | A1 | 7/2010 | Zhao et al. |
| 2010/0266171 | A1 | 10/2010 | Wendler |
| 2011/0046483 | A1 | 2/2011 | Fuchs |
| 2011/0060216 | A1 | 3/2011 | Foley et al. |
| 2011/0102549 | A1 | 5/2011 | Takahashi |
| 2012/0224311 | A1 | 9/2012 | Sutherland et al. |
| 2013/0060146 | A1 | 3/2013 | Yang et al. |
| 2013/0093738 | A1 | 4/2013 | Manus |
| 2013/0245461 | A1 | 9/2013 | Maier-Hein |
| 2013/0345718 | A1 | 12/2013 | Crawford et al. |
| 2014/0003572 | A1 | 1/2014 | Gregerson et al. |
| 2014/0139215 | A1 | 5/2014 | Gregerson et al. |
| 2014/0142426 | A1 | 5/2014 | Razzaque |
| 2014/0243614 | A1 | 8/2014 | Rothberg |
| 2014/0265182 | A1 | 9/2014 | Stanton et al. |
| 2014/0275760 | A1 | 9/2014 | Lee et al. |
| 2014/0275953 | A1 | 9/2014 | Gregerson et al. |
| 2014/0276001 | A1 | 9/2014 | Ungi et al. |
| 2015/0049083 | A1 | 2/2015 | Bidne |
| 2015/0143781 | A1 | 5/2015 | Agnihotri |
| 2015/0351860 | A1 | 12/2015 | Piron et al. |
| 2016/0030131 | A1 | 2/2016 | Yang et al. |
| 2016/0067007 | A1 | 3/2016 | Piron et al. |
| 2016/0081753 | A1 | 3/2016 | Kostrzewski |
| 2016/0095205 | A1 | 3/2016 | Cho et al. |
| 2016/0206379 | A1 | 7/2016 | Flett et al. |
| 2016/0225192 | A1 | 8/2016 | Jones et al. |
| 2016/0228204 | A1 | 8/2016 | Quaid et al. |
| 2016/0235402 | A1 | 8/2016 | Chowaniec |
| 2016/0302747 | A1 | 10/2016 | Averbuch |
| 2016/0354155 | A1 | 12/2016 | Hodges et al. |
| 2017/0007334 | A1 | 1/2017 | Crawford et al. |
| 2017/0116729 | A1 | 4/2017 | Stolka et al. |
| 2017/0172669 | A1 | 6/2017 | Berkowitz et al. |
| 2017/0189127 | A1 | 7/2017 | Weir |
| 2017/0215827 | A1 | 8/2017 | Johnson et al. |
| 2017/0231714 | A1 | 8/2017 | Kosmecki |
| 2017/0245940 | A1 | 8/2017 | Piron et al. |
| 2017/0245951 | A1 | 8/2017 | Crawford et al. |
| 2017/0258533 | A1 | 9/2017 | Crawford et al. |
| 2017/0281297 | A1 | 10/2017 | Tuma |
| 2018/0137690 | A1 | 5/2018 | Coffey |
| 2018/0279993 | A1 | 10/2018 | Crawford et al. |
| 2018/0303558 | A1 | 10/2018 | Thomas |
| 2018/0333207 | A1 | 11/2018 | Moctezuma De La Barrera |
| 2019/0380792 | A1 | 12/2019 | Poltaretskyi et al. |
| 2020/0253666 | A1 | 8/2020 | Spaelter et al. |
| 2020/0268473 | A1 | 8/2020 | Gregerson et al. |
| 2021/0378783 | A1 | 12/2021 | Gregerson et al. |

FOREIGN PATENT DOCUMENTS

| | | |
|---|---|---|
| EP | 3278758 A2 | 2/2018 |
| WO | 9832388 A2 | 7/1998 |
| WO | 2006039389 A2 | 4/2006 |
| WO | 2008039389 A1 | 4/2008 |
| WO | 2015177539 A1 | 11/2015 |
| WO | 2018049196 A1 | 3/2018 |

OTHER PUBLICATIONS

International Search Report from the Korean Intellectual Property; Office for PCT/US2017/050733, dated Feb. 20, 2018.

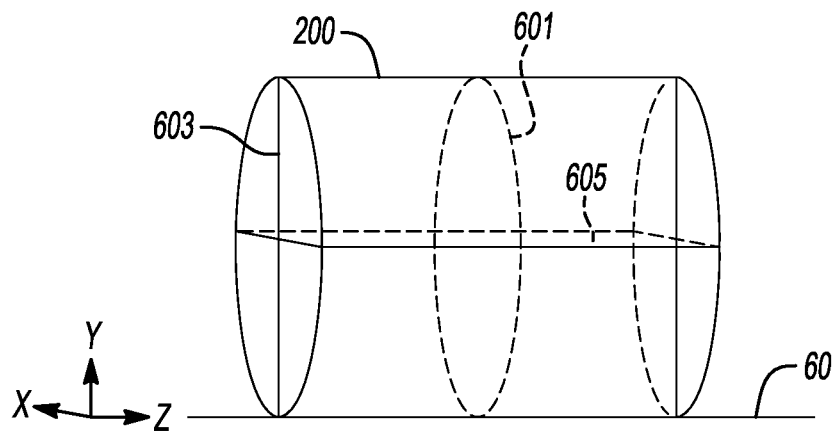
_Fig-6A_
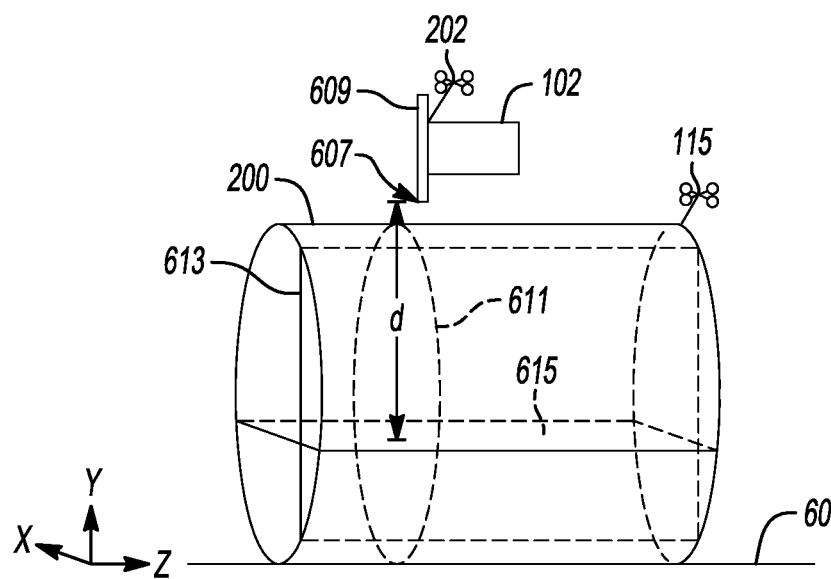
_Fig-6B_
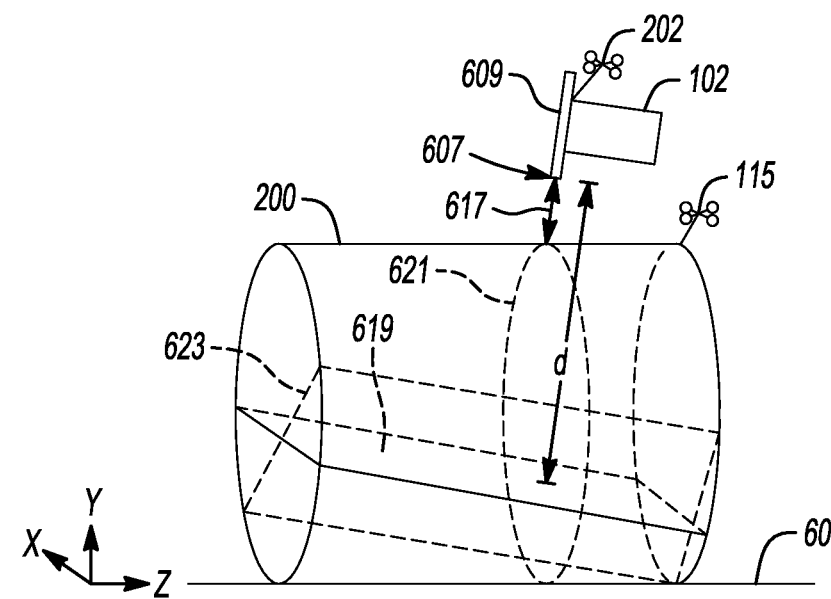
_Fig-6C_

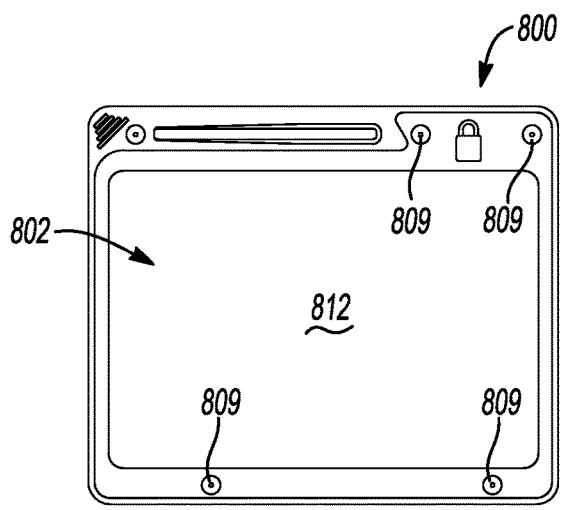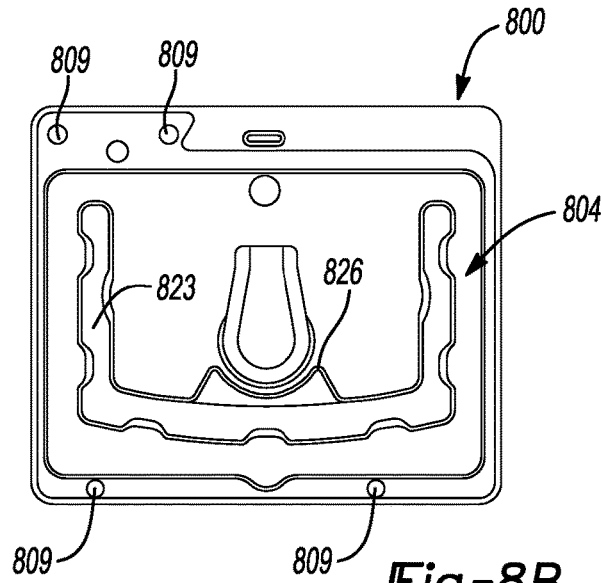
Fig-8A   Fig-8B
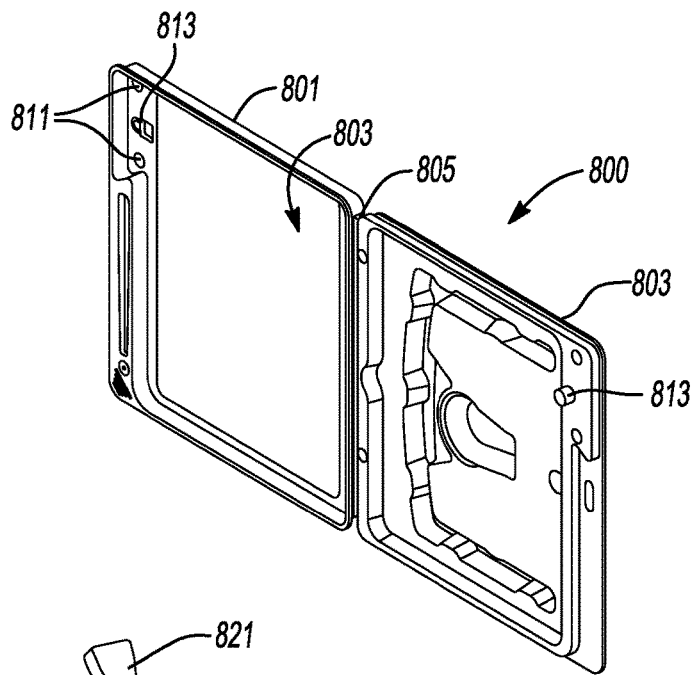
Fig-8C
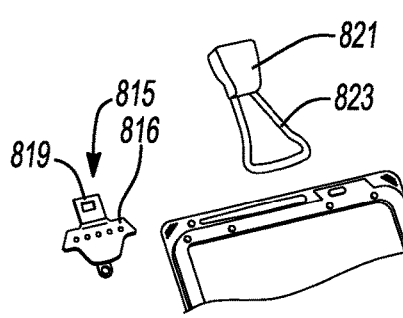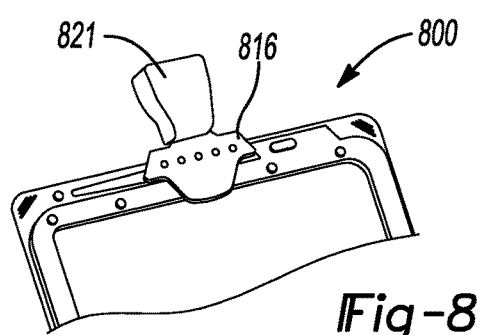
Fig-8D   Fig-8E

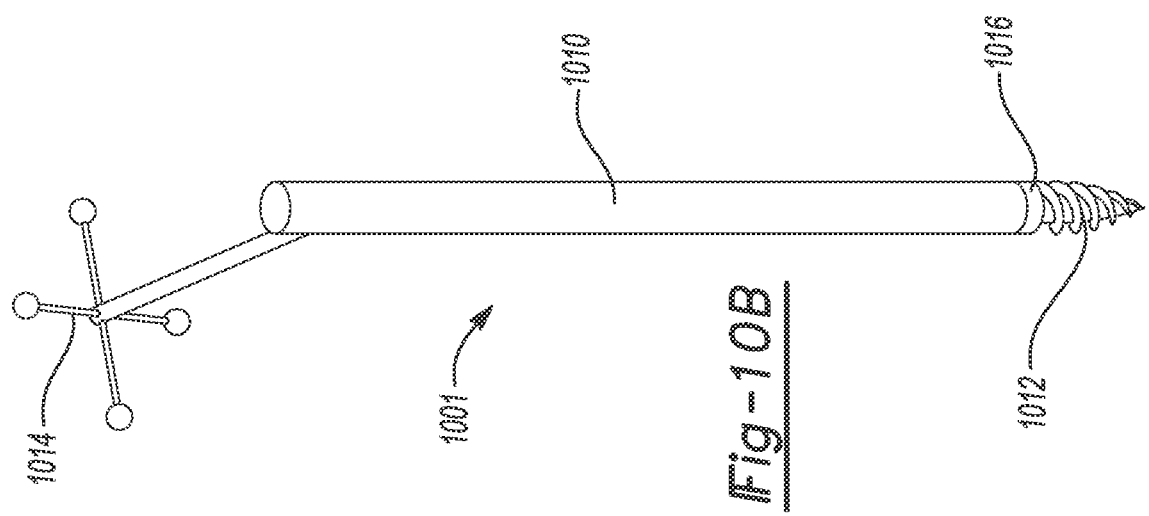

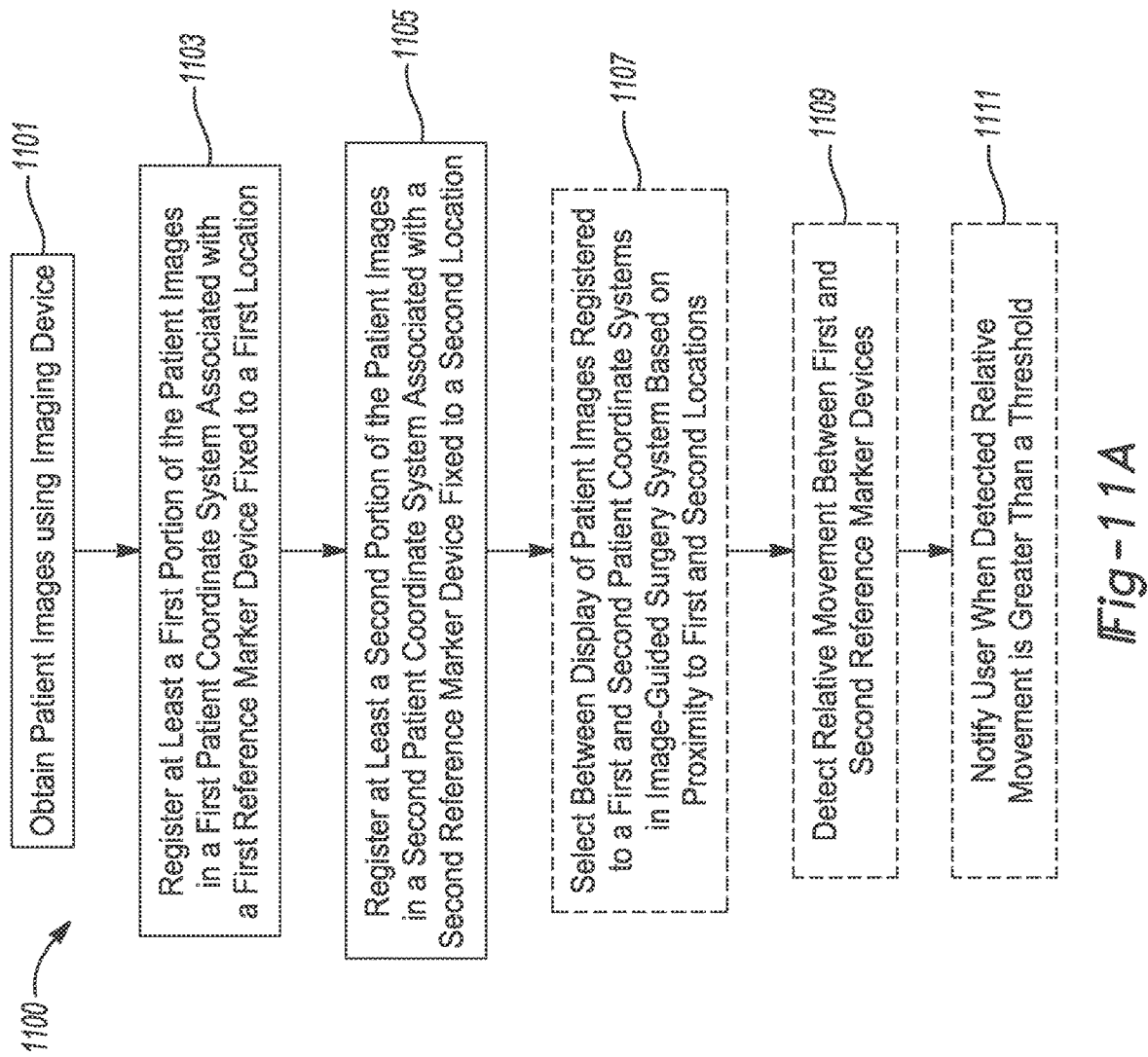

METHODS AND SYSTEMS FOR DISPLAY OF PATIENT DATA IN COMPUTER-ASSISTED SURGERY

CROSS-REFERENCE TO RELATED APPLICATIONS

This Application is a Continuation of U.S. patent application Ser. No. 17/410,024 filed on Aug. 24, 2021, which is a Continuation of U.S. patent application Ser. No. 16/839,829 filed on Apr. 3, 2020 and issued as U.S. Pat. No. 11,141,237 on Oct. 12, 2021, which is a Continuation of U.S. patent application Ser. No. 15/701,063 filed on Sep. 11, 2017 and issued as U.S. Pat. No. 10,653,495 on May 19, 2020, which claims priority to and benefit of U.S. Provisional Patent Application No. 62/385,552 filed on Sep. 9, 2016, the disclosures of each of which are hereby incorporated by reference in their entirety.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulators) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include methods and systems for performing computer-assisted image-guided surgery, including robotically-assisted surgery.

Embodiments include methods of displaying image data that include displaying image data of a patient on a display screen of a handheld display device, tracking at least one of a position and an orientation of the handheld display device with respect to the patient, and modifying at least a portion of the image data displayed on the display screen in response to a change in at least one of the position and orientation of the handheld display device with respect to the patient.

Further embodiments include methods of displaying image data that include displaying image data of a patient on a display screen, tracking at least one of a position and an orientation of an end effector of a robotic arm with respect to the patient, and modifying at least a portion of the image data displayed on the display screen in response to a change in at least one of the position and orientation of the end effector with respect to the patient.

Further embodiments include a sterile case for a handheld display device that includes a first portion defining a first surface of the case, the first portion having a window region in the first surface that is sized and shaped to correspond to a display screen of a handheld display device, a second portion defining a second surface of the case opposite the first surface, the first portion and the second portion defining a housing for receiving a handheld display device, the first and second portions having corresponding mating features that are engaged to secure a handheld display device within the housing, and a plurality of markers mounted to at least one of the first portion and the second portion and disposed in a pre-determined geometric pattern to enable at least one of the position and the orientation of the case to be tracked by a motion tracking system, the first portion and the second portion having sufficient rigidity to prevent relative movement of the plurality of markers.

Further embodiments include a display device for a robotic arm that includes a contoured viewing surface that extends around at least 50% of an outer periphery of a linkage member of the robotic arm, the display device displaying image data of a patient on the viewing surface.

Further embodiments include a robotic arm having a plurality of display devices mounted to different locations on the arm, wherein each display device may selectively display different indicators to indicate whether a particular portion of the arm may be moved in a handguided mode.

Further embodiments include a robotic arm having at least one display device located on a portion of the arm, wherein the at least one display device is configured to provide an indication of a direction in which the portion of the robotic arm may be moved in a handguided mode.

Further embodiments include methods for performing image-guided surgery using multiple reference marker devices fixed to a patient, the methods including obtaining patient images using an imaging device, registering at least a first portion of the patient images in a first patient coordinate system associated with first reference marker device fixed to a first location on the patient, registering at least a second portion of the patient images to a second patient coordinate system associated with a second reference marker device fixed to a second location on the patient, and selecting between display of patient images registered to the first patient coordinate system and display of patient images registered to the second patient coordinate system in an image guided surgery system based on a proximity to the first and second locations.

Further embodiments include methods for performing image-guided surgery using multiple reference marker devices fixed to a patient, the methods including obtaining patient images using an imaging device, tracking a first reference marker device fixed to a first location on the patient and a second reference marker device fixed to a second location on the patient using a motion tracking system, and displaying one or more patient images corresponding to a third location on the patient and a graphical depiction of a pose of an object tracked by the motion tracking system based on tracking data for both the first reference marker device and the second reference marker device in an image-guided surgery system.

Further embodiments include methods for performing image-guided surgery using multiple reference marker devices fixed to a patient, the methods including obtaining patient images using an imaging device, registering patient images to a patient coordinate system, displaying the patient images and a graphical depiction of a pose of an object tracked by a motion tracking system in the patient coordinate system using an image-guided surgery system, detecting a relative motion between a first reference marker device fixed to a first location on the patient and a second reference marker device fixed to a second location on the patient using the motion tracking system, determining whether the detected relative motion is consistent with an anatomic movement, and updating the display of the patient images and the graphical depiction of the pose of the object based on an estimation of the anatomic movement in response to determining that the detected relative motion is consistent with an anatomic movement.

Further embodiments include an image guided surgery system including a plurality of minimally-invasive reference markers fixed to different locations within a patient.

BRIEF DESCRIPTION OF THE DRAWINGS

Other features and advantages of the present invention will be apparent from the following detailed description of the invention, taken in conjunction with the accompanying drawings of which:

FIGS. 6A-6C schematically illustrate methods of displaying patient images in an image-guided surgery system based on a detected position and/or orientation of an end effector of a robotic arm according to an embodiment.

FIGS. 8A-8F illustrate a sterile case for a handheld display device according to an embodiment.

FIG. 10B illustrates a minimally-invasive reference marker device according to an embodiment.

FIG. 11A is a process flow diagram illustrating a method of performing image-guided surgery using multiple reference marker devices fixed to a patient.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
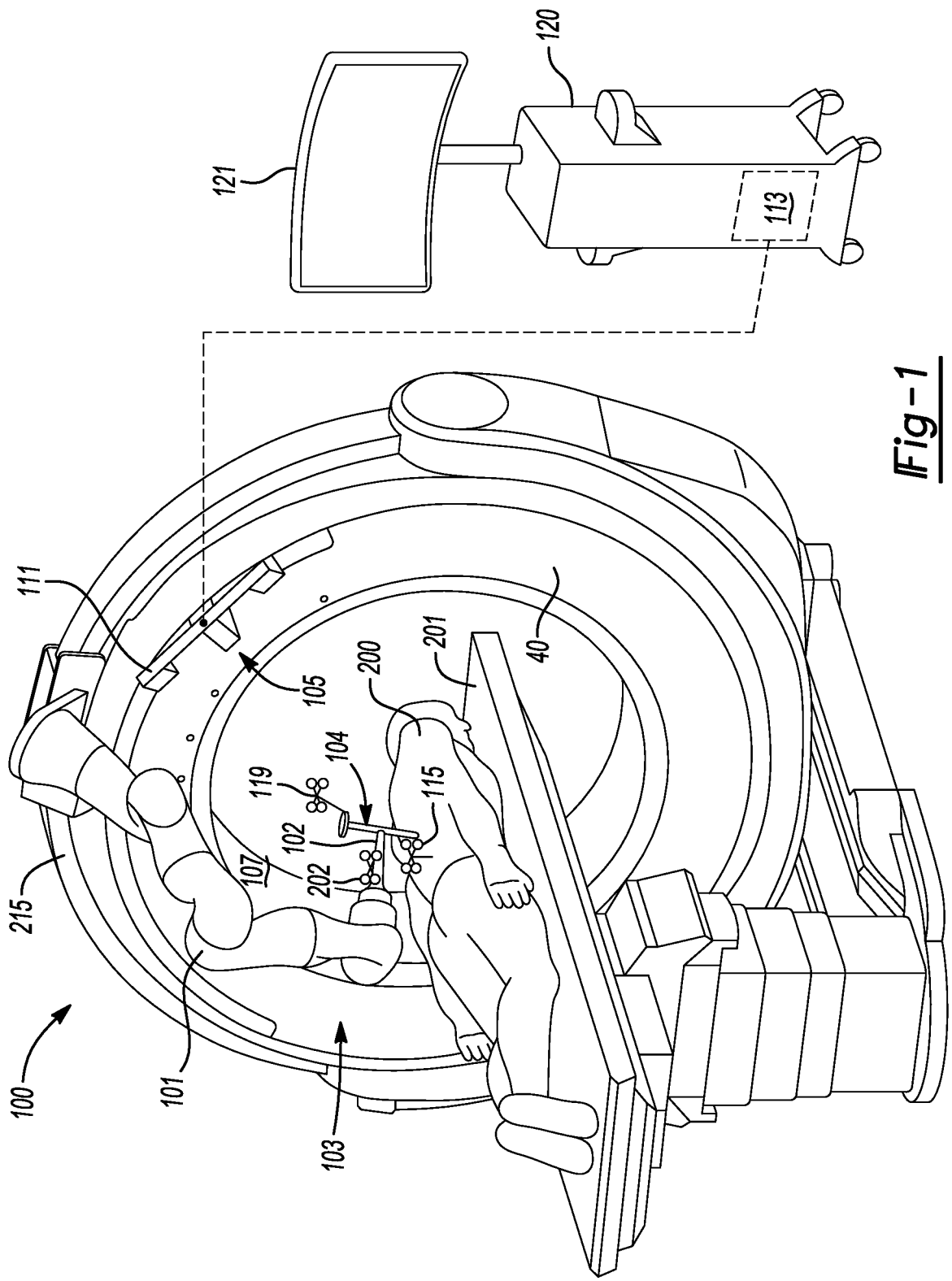
FIG. 1 is a perspective view of a system for performing robotically-assisted image-guided surgery according to an embodiment.

FIG. 1 illustrates a system 100 for performing computer-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi-joint arm that includes a plurality of linkages connected by joints having actuator(s) and optional encoder(s) to enable the linkages to rotate, bend and/or translate relative to one another in response to control signals from a robot control system. The robotic arm 101 may be fixed to a support structure at one end and may have an end effector 102 at the other end of the robotic arm 101.

The imaging device 103 may be used to obtain diagnostic images of a patient 200, which may be a human or animal patient. In embodiments, the imaging device 103 may be an x-ray computed tomography (CT) imaging device. The patient 200 may be positioned within a central bore 107 of the imaging device 103 and an x-ray source and detector may be rotated around the bore 107 to obtain x-ray image data (e.g., raw x-ray projection data) of the patient 200. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure), intra-operatively (i.e., during a surgical procedure) or post-operative (i.e., following a surgical procedure) by positioning the patient 200 within the bore 107 of the imaging device 103. In the system 100 of FIG. 1, this may be accomplished by moving the imaging device 103 over the patient 200 to perform a scan while the patient 200 may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient 200 may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient 200, and may translate away from the patient 200 to an out-of-the-way positon for performing a surgical procedure on the patient 200.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-Arm® surgical imaging system form Medtronic, plc. The imaging device 103 may also be a C-arm x-ray fluoroscopy device. In other embodiments, the imaging device 103 may be a fixed-bore imaging device, and the patient 200 may be moved into the bore of the device, either on a surgical support 60 as shown in FIG. 1, or on a separate patient table that is configured to slide in and out of the bore. Further, although the imaging device 103 shown in FIG. 1 is located close to the patient 200 within the surgical theater, the imaging device 103 may be located remote from the surgical theater, such as in another room or building (e.g., in a hospital radiology department).

The motion tracking system 105 in the embodiment of FIG. 1 includes a plurality of marker devices 119, 202, 315 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and 315 and a stereoscopic optical sensor device 111 that includes two or more cameras (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and 315 and received by the cameras. The marker devices 119, 202, 315 may each include three or more (e.g., four) reflecting spheres, which the motion tracking system 105 may use to construct a coordinate system for each of the marker devices 119, 202 and 315. A computer 113 may be coupled to the sensor device 111 and may determine the transformations between each of the marker devices 119, 202, 115 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, a reference marker device 115 (e.g., reference arc) may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 119 may be attached to surgical tools 104 to enable the tools 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria Innovation Inc. of Milwaukee, Wisconsin. Other tracking technologies, such as computer vision systems and/or magnetic-based tracking systems, may also be utilized.

Figure 2:
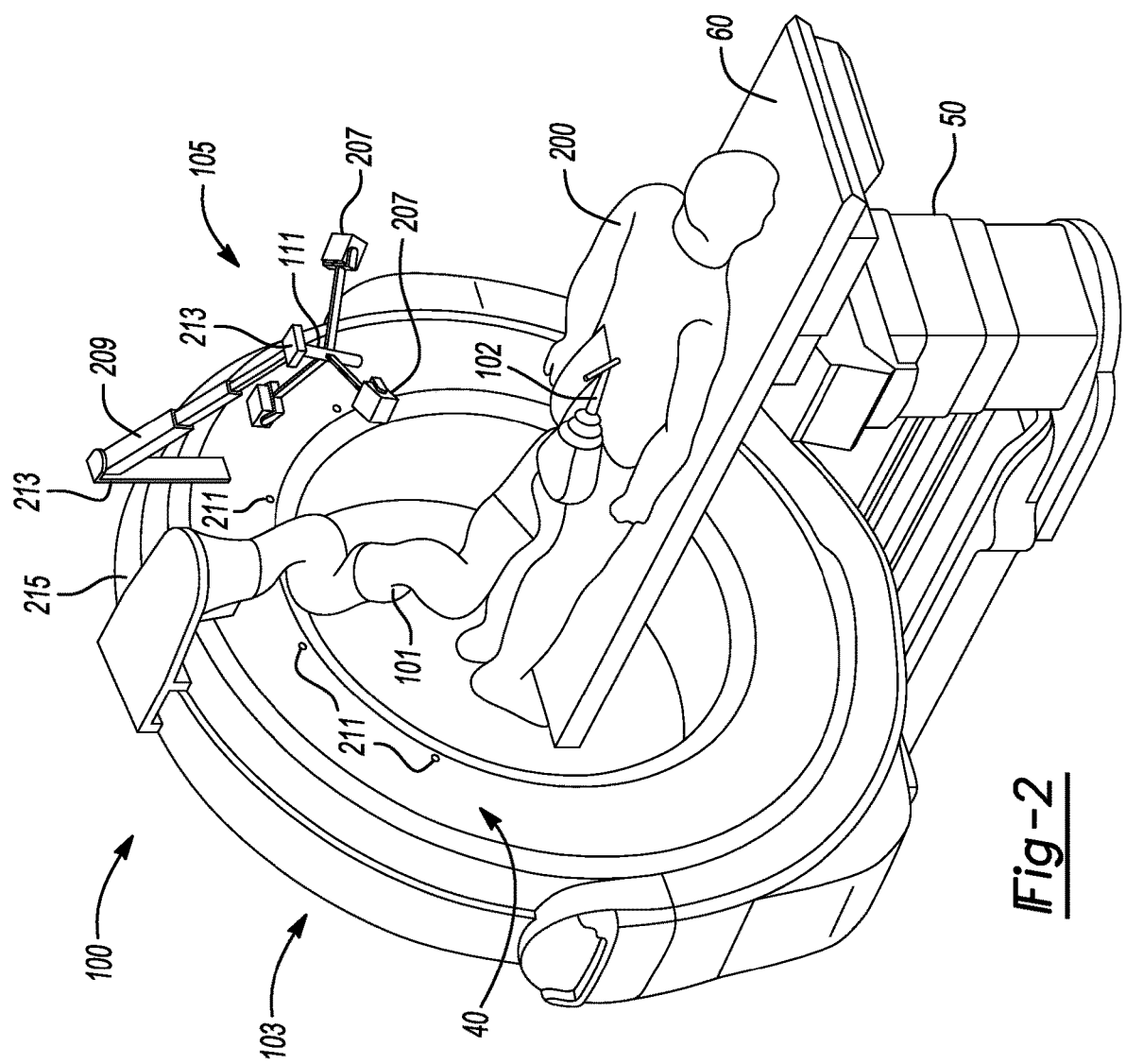
FIG. 2 shows an alternative embodiment of a system for performing robotically-assisted image-guided surgery having an optical sensing device for a motion tracking system on an arm extending from a gantry of an imaging system.

FIG. 2 illustrates an alternative embodiment in which the optical sensor device 111 includes a plurality of cameras 207 mounted to an arm 209 extending above the patient.200 surgical area. The arm 209 may be mounted to the imaging device 103 and may extend/retract in a telescoping manner to adjust the position of the sensor device 111. The arm 209 may also enable the sensor device 111 to pivot with respect to the arm 209 and/or the imaging device 103 (e.g., via one or more ball joints 213). The arm 209 may enable a user to adjust the position of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure. The positioning of the optical sensor device 111 on an arm 209 may also enable the cameras 207 to more easily view and track markers 211 that may be located on the imaging device 103, such as on the outer surface of the gantry 40, which may be used during automatic registration of patient images, as described further below.

The system 100 may also include a display device 121 as schematically illustrated in FIG. 1. The display device 121 may display image data of the patient's anatomy obtained by the imaging device 103. The display device 121 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display device 121, and may be shown overlaying the image data. In the embodiment of FIG. 1, the display device 121 is located on a mobile cart 120. A computer 113 for controlling the operation of the display device 121 may also be housed within the cart 120. In embodiments, the computer 113 may be coupled to the optical sensor device 111 and may also perform all or a portion of the processing (e.g., tracking calculations) for the motion tracking system 105. Alternatively, one or more separate computers may perform the motion tracking processing, and may send tracking data to computer 113 on the cart 120 via a wired or wireless communication link. The one or more separate computers for the motion tracking system 105 may be located on the imaging system 103, for example.

As shown in FIGS. 1-2, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted (see FIG. 2) may be mounted to the same or a similar support element 215 (e.g., curved rail) as the robotic arm 101. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. Although a single robotic arm 101 is shown in FIGS. 1 and 2, it will be understood that two or more robotic arms 101 may be utilized. In addition, various embodiments of a computer-assisted surgical method or system may include image-guided or navigation-supported surgery without the use of a robotic arm 101.

Figure 3:
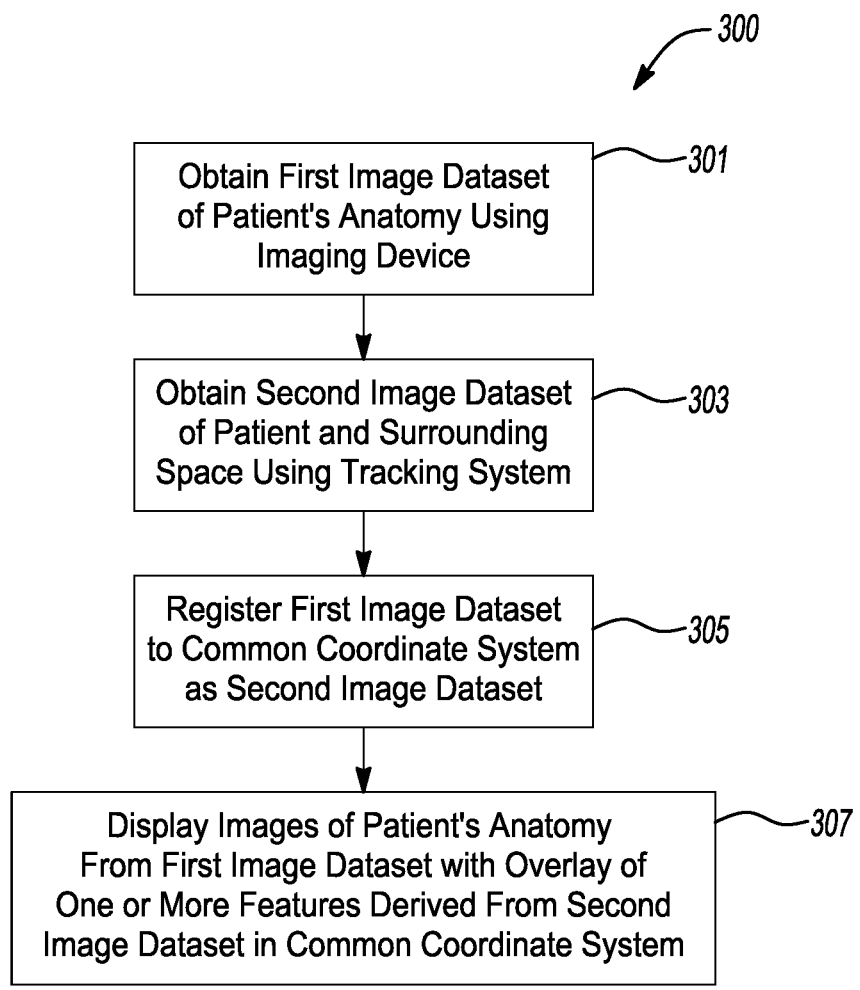
FIG. 3 is a process flow diagram illustrating a method for performing registration of patient image data for image-guided surgery.

FIG. 3 is a process flow diagram that illustrates a method 300 of registering patient images. Computer-assisted surgery techniques generally utilize a process of correlating a dataset representing a portion of the patient's anatomy that is to be operated on with the position of the patient at the time of the surgical intervention. The position of the patient may be determined based on a second image dataset which may include realtime camera image(s) from a motion tracking system 105 as described above. The correlation between these datasets may be accomplished computationally using software, and may be referred to as "patient registration." The registration method 300 of FIG. 3 may be implemented using one or more computing devices, such as computer 113 shown in FIG. 1.

In block 301 of method 300, a first image dataset of the patient's anatomy may be obtained using an imaging device, such as the imaging device 103 shown in FIGS. 1 and 2. The first image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The first image dataset may be stored electronically in a memory. The first image dataset may be in any suitable format, such as in a file format that conforms to the Digital Imaging and Communications in Medicine (DICOM) standard.

In block 303 of method 300, a second image dataset of the patient and the surrounding patient space may be obtained using a motion tracking system, such as the motion tracking system 105 shown in FIGS. 1 and 2. The second image dataset may indicate the current position and/or orientation of the patient. The second image dataset may include at least one image of a marker device that may be obtained using an optical sensing device 111 (e.g., cameras 207). The marker device (e.g., reference arc 115) detected by the optical sensing device 111 may be in a known fixed relationship with the surgically-relevant portion of the patient's anatomy. The motion tracking system 105 may determine the transformation between the marker device 115 and the optical sensing device 111 (e.g., using well-known triangulation techniques), and may thereby determine the transformation between the sensing device 111 (e.g., camera 207 position) and the surgically-relevant portion of the patient's anatomy.

The motion tracking system 105 may similarly determine transformations between each of the other marker devices (e.g., marker devices 119 and 202 in FIG. 1) and the optical sensing device 111. Each of the markers 115, 119 and 202 being tracked may then be placed within a common coordinate system. In embodiments, the common coordinate system may have an origin or zero point that is fixed relative to the surgically-relevant portion of the patient's anatomy, and may also be referred to the patient coordinate system.

In block 305 of method 300, the first image dataset may be registered to the common coordinate system as the second image dataset (e.g., the patient coordinate system). This may include performing a rigid transformation to map each pixel or voxel of the first image dataset into corresponding 3D coordinates (i.e., x, y, z coordinates) of the common coordinate system. A number of techniques may be utilized for registering multiple image datasets. In one non-limiting example of a registration process for x-ray CT imaging data, a pre-scan calibration process may be used to precisely calculate (e.g., within 1 mm) the transformation between the isocenter of the x-ray gantry 40 and the optical sensing device 111. A set of markers 211 (e.g., 3 or more, such as 4-6 markers) may be provided on the surface of the gantry 40, as shown in FIG. 2. The markers 211 may be within the field of view of the optical sensing device 111 to enable the gantry 40 position to be tracked by the motion tracking system 105. A calibration phantom (not shown for clarity) having a marker device (e.g., similar to marker device 115 in FIGS. 1 and 2) fixed thereto may be placed on the patient support 60 such that the marker device is also within the field of view of the optical sensing device 111. The motion tracking system 105 may determine the transformation between the gantry 40 coordinate system defined by the markers 211 and the optical sensing device 111 coordinate system as well as the transformation between the phantom coordinate system defined by the marker device on the phantom and the optical sensing device 111 coordinate system. These transformations may be used to determine the gantry-to-phantom transformation. The phantom may then be scanned using the imaging device 103. A set of elements (e.g., x-ray visible beads) that may be easily identified from the imaging data may be located in the phantom, where the geometry of these elements within the phantom coordinate system may be previously-known. An algorithm may be used to analyze the x-ray image data to identify the x-ray visible elements with respect to the center point of the image data, which corresponds to the isocenter of the gantry 40. Thus, the x-ray visible elements may be located in a coordinate system having an origin at the isocenter of the x-ray gantry 40, and the transformations between the isocenter and the phantom and the isocenter and the markers 211 on the gantry 40 may be calculated.

During a subsequent scan of the patient 200, the position and orientation of the patient 200 with respect to the isocenter of the imaging device 103 may be determined (i.e., by tracking the positions of the markers 211 on the gantry 40, which are known with respect to the isocenter, and the patient reference arc 115, which is known with respect to the surgically-relevant portion of the patient anatomy). This may enable the image data obtained during the scan to be registered into the patient coordinate system.

In an alternative embodiment, the position of the optical sensing device 111 may be known relative to the imaging system 103 with sufficient accuracy such that the image dataset of the patient's anatomy obtained using the imaging system 103 may be registered in the common coordinate system of the patient without the motion tracking system 105 needing to track the position or orientation of the imaging system 103. In embodiments, separate markers 211 on the gantry 40 of the imaging system 103 as shown in FIG. 2 may not be required or used. In some embodiments, the position of the optical sensing device 111 (e.g., the position of each of the cameras 207 as shown in FIGS. 1 and 2) may be known relative to the isocenter of the gantry 40 of the imaging system 103, such as via a calibration process that may be performed at the factory or during installation or precalibration of the system. The gantry 40 and/or the optical sensing device 111 may include keying features (e.g., high-precision bolt patterns) where the optical sensing device 111 attaches to the gantry 40 to ensure that the position of the sensing device 111 on the gantry 40 remains accurately fixed. In embodiments where the camera(s) 207 may be movable relative to the gantry 40, high-precision encoders may precisely record and correct for any changes in camera position/orientation relative to the isocenter of the gantry 40. During imaging scans, the optical sensing device 111 may track the position and orientation of the patient 200 with respect to the camera position, which is in a known, fixed geometric relationship with the isocenter of the imaging device 103. The image data obtained during a scan may thus be registered into the common coordinate system of the patient without needing to first perform a calibration scan on a phantom, as described above.

In block 307 of method 300, images of the patient's anatomy from the first image dataset may be displayed with an overlay of one or more features derived from the second image dataset in the common coordinate system. The images may be displayed on a suitable display device, such as display device 121 shown in FIG. 1. The images of the patient's anatomy may include 2D slices of a three-dimensional image dataset (e.g., a tomographic reconstruction) and/or a 3D volume rendering of all or a portion of the image dataset. In embodiments, images obtained using multiple imaging devices or imaging modalities may be fused and displayed in a common coordinate system. For example, the first image dataset of the patient's internal anatomy may be an x-ray CT scan. Another image dataset of the patient's internal anatomy, such as an MRI scan, may be combined with the x-ray CT data and displayed on the display device 121. The MRI scan data may be registered into the common coordinate system using a similar registration process as described above. Alternately or in addition, an algorithm for matching landmarks or fiducials identifiable from both image datasets may be used to merge the datasets for display.

The one or more features derived from the second image dataset that may be displayed overlaying the images of the patient's anatomy may include graphical depictions of a tool 104, an end effector 102 or another object that is tracked by the motion tracking system 105. The graphical depiction may be based on a known geometry of the tool 104, end effector 102 or other object. The graphical depiction may be a rendering of the actual size and shape of the object or may be a depiction of select features of the object, such as a location of a tip end of the object and/or an orientation of the object. The graphical depiction may also indicate a trajectory defined by the object (e.g., a ray extending from a tip end of the object into the patient) and/or a target point within the patient's anatomy that may be defined based on the position and/or orientation of one or more objects being tracked. In various embodiments, the tool 104 may be a pointer. The tool 104 may also be a surgical instrument, such as a needle, a cannula, a tool for gripping or cutting, an electrode, an implant, a drill bit, a screw, a screw driver, a radiation source, a drug and an endoscope. In embodiments, the end effector 102 of the robotic arm 101 may include a hollow tube or cannula that may be configured to hold one or more tools, such as a surgical instrument, and may be used to guide an instrument as it is inserted into the patient's body. Alternately, the end effector 102 itself may be or may include an instrument that may be inserted into the patient's body.

The motion tracking system 105 may repeatedly acquire new images from the optical sensing device 111, and the relative positions and/or orientations of objects within the field of view of the optical sensing device 111 may be updated with each acquisition of new images from the optical sensing device 111. The display device 121 may be updated to reflect any change(s) in the position and/or orientation of the objects within the common coordinate system (e.g., relative to the patient reference arc 115), which may include adding additional graphical elements to depict new objects that are moved within the field of view of the optical sensing device 111 and removing graphical depictions of objects when they are no longer within the field of view of the optical sensing device 111. In some embodiments, the optical sensing device 111 may include a motorized system to enable the position and/or orientation of the camera(s) 207 to move to maintain the surgical area within the center of the field of view of the camera(s) 207.

Figure 4:
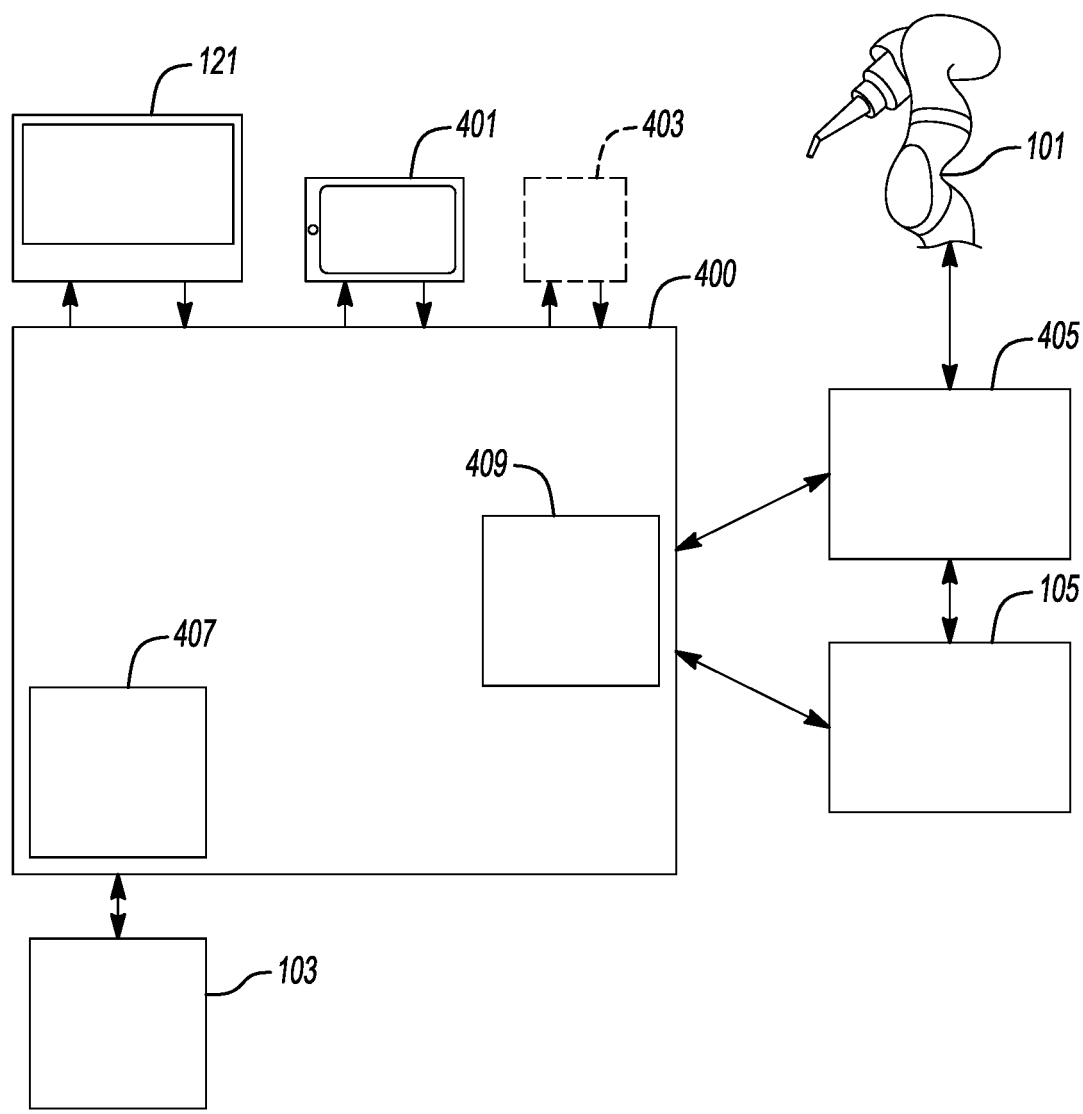
FIG. 4 is a block diagram schematically illustrating a system for image-guided surgery according to an embodiment.

FIG. 4 is a component block diagram of an image-guided surgery system 400 according to an embodiment. The system 400 may be implemented using one or more computing devices, such as computer 113 shown in FIG. 1. The system 400 may be operatively coupled to a first display device 121, which may include a monitor that is fixed to a cart 120 or other structure (e.g., wall, ceiling, floor, imaging device, etc.) within the operating suite. The system 400 may also be operatively coupled to at least one additional display device 401, which may be a handheld computing device, as described in further detail below. The system 400 may also include an audio input/output component 403, which may include a speaker or other output component for outputting audible signals (e.g., audio instructions, alerts, etc.) and/or a microphone or other input component for receiving audio inputs (e.g., voice commands) that may be interpreted by the system 400. The system 400 may be implemented at least partially in software and may be based on one or more of the Image-Guided Surgery Toolkit (IGSTK), Visualization Toolkit (VTK) and Insight Segmentation and Registration Toolkit (ITK) development frameworks.

The system 400 may be configured to receive and store imaging data 407 (e.g., DICOM data) collected by an imaging device 103. The imaging data 407 may be received directly from the imaging device 103 or may be retrieved from another source, such as a remote server. The imaging data 407 may be imaging data that is obtained prior to a surgical procedure (e.g., pre-operative image data) and/or imaging data that is obtained during a surgical procedure (e.g., intra-operative image data). In embodiments, the system 400 may be configured to display the most-current image data 407 collected by the imaging device 103. The image data 407 may be registered to a common coordinate system as the tracking data 409 from the motion tracking system 105 in accordance with a registration method such as method 300 described above with reference to FIG. 3.

The system 400 may also receive tracking data 409 from a motion tracking system 105. The system 400 may be configured to repeatedly read the tracking data from the motion tracking system 105 indicating the current position/orientation of the patient and any other objects tracked by the motion tracking system 105. The system 400 may read the tracking data at a frequency (e.g., refresh rate) of greater than 100 Hz (e.g., 240 Hz). In embodiments, the tracking data from the motion tracking system 105 may include data to enable the system 400 to identify particular objects from within the tracking data. For example, each marker device (e.g., marker devices 115, 202 and 119 in FIG. 1) may include a unique characteristic (e.g., a unique geometric pattern of reflective markers, a unique flash pattern of active markers, etc.) to enable the marker device to be identified. These unique characteristics of the marker devices may be registered with particular objects or tools (e.g., associated with a particular object or tool in a database) by the system 400. The unique characteristics of the marker devices may be pre-registered in the system 400 and/or may be registered to particular objects or tools during the course of a surgical procedure. The system 400 may also include a library of graphical elements that may be associated with particular objects or tools (e.g., in a database). The system 400 may display graphical elements associated with the objects or tools being tracked by the motion tracking system 105 in the common coordinate system with the image data on the display(s) 121, 401.

The system 400 may include a user-interface component that may control the display of system information and/or graphical user interface elements on the display(s) 121 and 401. The system 400 may further process and implement user commands received from user interface devices. A user interface device, may include, for example, a touchscreen user interface which may be integrated with a display device 121,401. In embodiments, a user interface device may alternately or additionally include one or more of a button, a keyboard, a joystick, a mouse, a touchpad, etc. which may be located on a display device 121, 401 and/or on a workstation (e.g., a workstation located on a cart 120). In embodiments, the user interface device(s) may also include a microphone (e.g., audio input/output component 403) that may receive voice commands that may be interpreted by the system (e.g., using voice recognition software). The user commands received via one or more user input devices may enable a user to control various functions of the system 400, such as changing what is shown on the display(s) 121,401 (e.g., displaying different image datasets, displaying different slice(s) and/or different 3D rendering(s) within an image dataset, zooming in or out of an image, displaying different menu options, returning to a home screen, etc.). In embodiments, the user commands may enable a user to set one or more trajectories and/or target locations within the patient's anatomy. The system 400 may store the positions and/or orientations of user-defined trajectories or target locations within the common coordinate system, and may display graphical representations of such trajectories or target locations on the display(s) 121, 401.

The user commands received by the system 400 may also include commands for controlling the operation of other components, such as the imaging device 103, the motion tracking system 105 and/or a robotic arm 101. For example, for a robotically-assisted surgical procedure, the user command may include an instruction to move a robotic arm 101 to a particular position and/or orientation. The instruction to move the robotic arm 101 may be based on a user interaction with image data of the patient's anatomy that is displayed on a display device 121,401. For example, the user may use the display device 121, 401 to define a particular trajectory with respect to the patient's anatomy and may send an instruction for the robotic arm 101 to move such that the end effector 102 of the robotic arm 101 is positioned along the defined trajectory.

A robotic control system 405 may control the movement of one or more robotic arms 101. The robotic control system 405 may receive sensor data indicating the current parameters of the robotic arm 101 (e.g., robot position, joint angles, measured axis forces, motor currents) and may send motor control signals to drive the movement of the arm 101. In embodiments, the motion tracking system 105 may track the position of the robotic arm 101 (e.g., via marker device 202 on end effector 102 as shown in FIG. 1) to determine the position of the end effector 102 within the common coordinate system of the patient. A control loop, which may be executed using the image-guided surgery system 400, the motion tracking system 105 and/or the robotic control system 405, may continuously read the tracking data and the robot parameter data and may send instructions to the robotic control system 405 to cause the robotic arm 101 to move to a desired position and orientation.

In various embodiments, display device 121 may be a primary display device (e.g., a monitor) that may be connected to the image-guided surgery system 400 by a wired or wireless link. In one embodiment, the system 400 may stream video data to the display device 121 over a suitable video data interface (e.g., an HDMI interface) and may also exchange other signals with the display device over a separate data connection (e.g., a USB connection).

In various embodiments, display device 401 may be a handheld computing device. As used herein, "handheld computing device" and "handheld display device" are used interchangeably to refer to any one or all of tablet computers, smartphones, pendant controllers, cellular telephones, personal digital assistants (PDA's), netbooks, e-readers, laptop computers, palm-top computers, wearable computers, and similar portable electronic devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands. A handheld display device 401 may generally be smaller and lighter than the primary display device 121 (e.g., monitor), and may in certain embodiments be referred to as a secondary display device. In some embodiments, display device 401 may be a mirror of display device 121 and may display all or a portion of the same information as is shown on display device 121. Alternately, display device 401 may display different information than is shown on display device 121. In some embodiments, display device 121 may be omitted, and handheld display device 401 may be the only display device operably connected to the image-guided surgery system 400. In such a case, display device 401 may be referred to as the primary display device. Further, although a single handheld display device 401 (i.e., a tablet computer) is shown in FIG. 4, it will be understood that multiple handheld display devices 401 may be simultaneously connected to and used with the system 400.

The handheld display device 401 may be coupled to the image-guided surgery system 400 by a wired or wireless communication link. In one embodiment, the handheld display device 401 may communicate with the system 400 over a wireless communication interface. The system 400 may stream digital video data (e.g., high-definition video) for display on the handheld display device 401, such as over a wireless local area network (WLAN) connection, including a IEEE 801.11 (e.g., WiFi) connection. The system 400 may also exchange other signals with the handheld display device 401 (e.g., control signals from the system 400 and/or user commands received at a user interface, such as a touchscreen, on the display device 401) over a wireless connection. The system 400 and the display device 401 may communicate over any suitable wireless protocol or standard, such as over a IEEE 802.15x (e.g., a BLUETOOTH®) connection.

An image-guided surgical system 400 according to various embodiments may provide a plurality of modes for displaying patient information. For example, a first display mode may include displaying a 3D image dataset (e.g., an x-ray CT, MRI, sonogram, PET or SPECT image dataset) in multiple two-dimensional slices corresponding to anatomic planes (e.g., axial, sagittal, coronal planes) transecting the patient. This is illustrated in the screenshot of a display device shown in FIG. 5. The display device may be a display device 121 (e.g., monitor) or a handheld display device 401 as shown in FIG. 4. The display screen 500 in this example illustrates four different patient images in four quadrants of the display screen 500. Three of the quadrants (i.e., top left, top right and bottom left quadrants of display screen 500) depict different two-dimensional slices 501, 503, 505 of CT image data. A fourth quadrant (i.e., lower left quadrant of display screen 500) includes a 3D volume rendering 507 illustrating a "virtual" view of anatomic feature(s) (e.g., bony structures or other discrete internal anatomic features). The two-dimensional slices 501, 503, 505 correspond, respectively, to views taken along axial, sagittal and coronal planes through the patient 200. This is illustrated schematically in FIG. 6A, which illustrates a portion of the patient 200 lying flat on a support surface 60 (i.e., along the patient or z-axis in FIG. 6A). The axial slice 501 depicts a cross-section through the patient 200 in the x-y plane 601 (i.e., transverse to the patient or z-axis). Any arbitrary axial slice 501 through the patient 200 may be shown on the display screen 500. In one embodiment, the display screen 500 may display a default axial slice 501 which may correspond to the slice passing through the center of the reconstructed volume. The sagittal slice 503 depicts a cross-section through the patient 200 in the y-z plane 603 (i.e., separating the right and left sides of the patient 200), as shown in FIG. 6A. Any arbitrary sagittal slice 503 within the reconstructed volume may be shown on the display screen 500. In one embodiment, the display screen 500 may display a default sagittal slice 503 which may correspond to a mid-sagittal slice (i.e., passing through the midline of the patient) or a slice through the center of the reconstructed volume. The coronal slice 505 depicts a cross-section through the patient 200 in the x-z plane 605 (i.e., parallel to the patient table 60 and separating the front and back sides of the patient 200), as shown in FIG. 6A. Any arbitrary coronal slice 505 within the reconstructed volume may be shown on the display screen 500. In one embodiment, the display screen 500 may display a default coronal slice 505 which may correspond to a mid-coronal slice (i.e., transecting the anterior and posterior halves of the patient 200) or a slice through the center of the reconstructed volume. In some embodiments, the default coronal slice 505 that is displayed may be based on a particular anatomic feature in the image data (e.g., through a portion of the patient's spine for spine surgery) or in a plane at a particular height in the y-axis direction (e.g., at a particular distance from the patient table 60 and/or a depth from the top of the patient).

Figure 5:
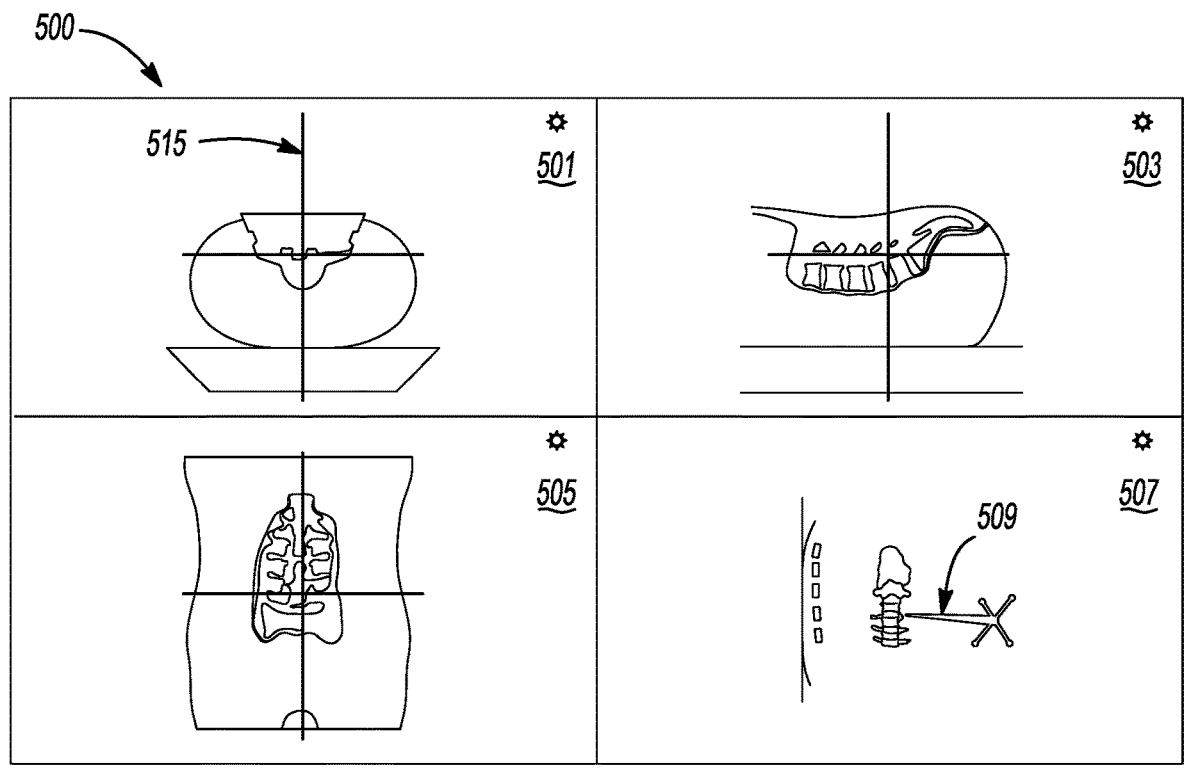
FIG. 5 illustrates a display screen of a display device in an image-guided surgery system according to an embodiment.

The display screen 500 may also display graphical elements illustrating the relationship of each slice 501, 503, 505 relative to the other slices shown on the display screen 500. For example, as shown in FIG. 5, the axial slice 501 image data may include an overlay of a cross pattern 515 showing the intersection of the axial slice 501 with the planes corresponding to the sagittal and coronal slices 503 and 505 shown on the display screen 500. Similar cross patterns 515 may be displayed overlaying the display of image data in the sagittal and coronal slices 503 and 505. The display screen 500 may also include graphical representations or renderings of other objects or tools tracked by the motion tracking system 105. In the example of FIG. 5, a graphical representation of a tool 509 is shown in the lower right quadrant of the display screen 500. The graphical representation of the tool 509 may illustrate the position and orientation of the tool relative to the anatomic features depicted in the 3D volume rendering 507. Similar graphical elements may be displayed in the 2D slice images 501, 503 and 505 to illustrate the position and/or orientation of one or more objects with respect to the patient.

It will be understood that the four-quadrant view shown in FIG. 5 is one possible implementation of a display of patient information on a display device 121, 401. Other possible display modes are possible. For example, rather than illustrating multiple different images (e.g., slices) from a patient image dataset (e.g., reconstructed volume), the display screen 500 may show only a single image (e.g., a single axial, sagittal or coronal slice 501, 503, 505 or a single 3D volume rendering 507). The display screen 500 may illustrate only two slices corresponding to different anatomic planes (e.g., axial and sagittal, axial and coronal, or sagittal and coronal slices), or may illustrate a single slice along with a 3D volume rendering. In some embodiments, the display screen 500 may illustrate multiple two-dimensional slices corresponding to the same anatomic planes (e.g., multiple axial, sagittal and/or coronal slices taken through different sections of the reconstructed volume) and/or multiple 3D volume renderings viewed from different angles. The different images and display modes of the display screen 500 may be customizable based on user selections, which may be made via a user input device and/or user voice commands. In embodiments, the user may be able to select (e.g., scroll through) different patient images, such as sequentially illustrating multiple axial, sagittal and/or coronal slices taken through different sections of the reconstructed volume, or sequentially illustrating multiple 3D volume renderings viewed from different angles. The user may also have the capability to control the magnification of images, such as by zooming into or out from a particular portion of an image shown in the display screen 500. The user may control the selection of patient images for display using a user input device, voice commands and/or via a separate tool, such as a pointer device.

In various embodiments, at least a portion of the image data displayed on the display device 121, 401 may be modified in response to a change in at least one of the position and orientation of the robotic arm 101 with respect to the patient 200. This is schematically illustrated in FIG. 6B, which illustrates an end effector 102 of a robotic arm 101 positioned over a patient 200. The end effector 102 may have a marker device 202 that enables the end effector 102 to be tracked by the optical sensing device 111 of the motion tracking system 105, as described above. Another marker device 115 may be fixed to the patient 200 so that the position and/or orientation of the end effector 102 may be tracked relative to the patient coordinate system. The motion tracking system 105 may determine the location of a portion of the end effector 102, such as a tip end 607 of the end effector (e.g., a tip of a cannula 609 or other tool holder), which may have a known fixed geometric relationship to the marker device 202, within the patient coordinate system. The display screen 500 of the display device 121, 401 may display different portions of the patient image dataset (e.g., a three-dimensional tomographic reconstruction) based on the detected position of the tip end 607 of the end effector 102.

In the embodiment of FIG. 6B, for example, the display screen 500 may depict the two-dimensional axial slice 611 of the image dataset that corresponds to the axial position of the tip end 607 of the end effector 102 with respect to the patient 200 (e.g., the position of the tip end 607 along the length of the patient 200 in the z-axis direction). As the robotic arm 101 moves with respect to the patient 200, the display screen 500 may be updated to show the axial slice(s) 611 corresponding to the current position of the tip end 607 of the end effector 102 with respect to the patient 200.

Similarly, the display screen 500 may depict the two-dimensional sagittal slice 613 of the image dataset that corresponds to the sagittal position of the tip end 607 of the end effector 102 with respect to the patient 200 (e.g., the position of the tip end 607 along the width of the patient 200 in the x-axis direction). As the robotic arm 101 moves with respect to the patient 200, the display screen 500 may be updated to show the sagittal slice(s) 613 corresponding to the current position of the tip end 607 of the end effector 102 with respect to the patient 200.

The display screen 500 may also depict a two-dimensional coronal slice 615 based on the position of the tip end 607 of the end effector 102 with respect to the patient 200. In one embodiment, the display screen 500 may depict a coronal slice 615 of the image dataset that is offset from the position of the tip end 607 (i.e., in the y-axis direction) by a pre-determined distance, d. The off-set distance, d, may be a user-adjustable parameter. As the robotic arm 101 moves with respect to the patient 200, the display screen 500 may be updated to show the coronal slice(s) corresponding to the position of the tip end 607 offset by the pre-determined distance, d.

In further embodiments, the display screen 500 may display oblique two-dimensional slices of the patient image dataset (e.g., a three-dimensional tomographic reconstruction) based on the detected position and orientation of the tip end 607 of the end effector 102. This is schematically illustrated by FIG. 6C. The tip end 607 of the end effector 102 may have up to six degrees of freedom with respect to the patient 200—i.e., displacement along the x, y and z axes as well as pitch, yaw and roll rotation about these axes. The motion tracking system 105 may determine both the position (i.e., displacement) and orientation (i.e., rotation) of the tip end 607 of the end effector 102 with respect to the patient coordinate system. In embodiments, the display screen 500 may display two-dimensional slices through the patient image dataset with reference to both the position and orientation of the tip end 607 of the end effector 102. In embodiments, the display screen 500 may display axial, sagittal and coronal slices through the image dataset based on the position of the tip end 607 of the end effector 102 as described above with reference to FIG. 6B, where each of the slices may be rotated relative to the anatomic planes of the patient 200 based on the orientation of the tip end 607 of the end effector 102.

This is schematically illustrated by FIG. 6C, which shows an end effector 102 positioned over and rotated with respect to the patient 200. In this embodiment, the trajectory defined by the cannula 609 of the end effector 102 is rotated to an oblique angle with respect to the patient 200 in one or more rotational degrees of freedom. In this example, the oblique "coronal" slice through the patient 200 may correspond to a plane 619 that is normal to a ray 617 projected forward from the tip end 607 of the end effector 102 along the trajectory defined by the cannula 609 and that is off-set from the tip end 607 by a pre-determined distance, d. As in the embodiment of FIG. 6B, the off-set distance, d, may be a user-adjustable parameter. The ray 617 may further define the intersection of the planes 621 and 623 of the oblique "axial" and "sagittal" slices, respectively, which may be orthogonal to each other and to the plane 619 of the oblique "coronal" slice. Put another way, the tip end 607 of the end effector 102 may define an end effector coordinate system having a first axis (e.g., a y' axis) extending towards the patient along the direction of the ray 617, and mutually-perpendicular second and third axes (e.g., z' and x' axes) extending from the tip end 607 in a plane normal to the first axis, where the planes 621, 629 and 619 of the oblique "axial," "sagittal" and "coronal" slices may be based on the position and rotation of the end effector coordinate system with respect to the patient coordinate system. The oblique "axial", "sagittal" and/or "coronal" slices corresponding to planes 621, 629 and 619, respectively, may be shown on the display screen 500.

As the robotic arm 101 moves with respect to the patient 200, the display screen 500 may be updated to show the oblique axial, sagittal and/or coronal slices based on the current position and orientation of the end effector 102 with respect to the patient 200.

In various embodiments, the intersection of the three image planes (i.e., axial, sagittal and coronal) may coincide with a target position within the patient's body. The surgeon may use the display panel 500 as a "virtual cutting tool" to move through the various slices/views of the patient image volume and to identify and select a target region for a surgical intervention. In embodiments, the surgeon may move through the various views of the patient image volume by moving the robotic arm 101 with respect to the patient 200, as discussed above with reference to FIGS. 6B and 6C. The display panel 500 may also enable the surgeon to visualize multiple trajectories or paths extending from the patient's skin surface through the patient's anatomy to the target position. In the embodiment of FIG. 6C, for example, the surgeon may view a set of trajectories in multiple planes by moving the tip end 607 of end effector 102 of the robotic arm 101 over a virtual spherical surface centered on a particular target point within the patient 200. As discussed above, a ray 617 projected forward from the tip end 607 of the end effector 102 may define the intersection between multiple image slices shown on the display screen 500, and may further define a unique trajectory through the patient 200. The pre-determined displacement distance, d, from the tip end 607 of the end effector 102 may define the target position along the unique trajectory.

The user (e.g., a surgeon) may be able to set one or more target positions and/or trajectories within the patient 200. There may be a variety of ways to set a target position or a target trajectory. For example, the surgeon may move through different views of the patient image data by moving a robotic arm 101 as discussed above or by using another tool (e.g., a pointer device). Alternately, the surgeon may directly manipulate and interact with the displayed image data to identify a particular target or trajectory, such as using a workstation computer. A particular target point or trajectory may be set by the system 400 in response to an input event, which may include, for example, a voice command, a touch event on a touchscreen interface, and/or an input on a user interface device (e.g., a keyboard entry, a mouse click, a button push, etc.). In embodiments, the surgeon may set a target position and/or trajectory by interacting with image data displayed on a display device, such as display devices 121 and/or 401. For example, the surgeon may define a target point and/or trajectory in the patient 200 by selecting one or more points on a display screen 500 of a display device 121,401 (e.g., marking the points using a stylus, a cursor or mouse pointer, or a touch on a touchscreen user interface). To define a trajectory, for instance, the user may select two or more points in the image data (e.g., a target point and an entrance point on the skin of the patient). In embodiments, the user may be able to make fine adjustments to a selected target point and/or trajectory using any suitable user interface device. Multiple target points and/or trajectories may be set and saved in a memory (e.g., in an image-guided surgery system 400 as illustrated in FIG. 4), where each target point and/or trajectory may be saved in association with a unique identifier (e.g., file name).

In embodiments, the display screen 500 may display graphical element(s) overlaying the image data corresponding to one or more target positions and/or trajectories that are set by the user. For example, defined target positions may be illustrated as identifiable dots or points in the image data, which may be color coded and/or labeled on the display screen 500 to enable easy visualization. Alternately or in addition, defined trajectories may be depicted as identifiable lines or line segments in the image data, which may be similarly color coded and/or labeled. As discussed above, the display screen 500 may also display graphical elements associated with particular tools or objects, including invasive surgical tools or instruments, that are tracked by the motion tracking system 105. In embodiments, the display screen 500 may depict at least a portion (e.g., a tip end) of a surgical instrument as it is inserted into the patient 200, which may enable the surgeon to track the progress of the instrument as it progresses along a defined trajectory and/or towards a defined target position in the patient 200.

In various embodiments of a robotically-assisted surgical system, a robotic arm 101 may be operated in a number of different operating modes. For example, the robotic arm 101 may operate in a hand guiding mode in which the movement of the robotic arm 101 may be controlled based on a force applied by a user to the arm (e.g., using torque and/or force sensing feedback to a robotic control system 405 as shown in FIG. 4). The robotic arm 101 may also operate in an autonomous mode in which the robotic arm 101 moves to particular poses in response to control signals from the robotic control system 405 (e.g., in accordance with a robotic motion planning algorithm and/or in response to signals from a separate user controller device, such as a joystick controller). The robotic arm 101 may also operate in a static or braked mode in which the robotic arm 101 may hold a particular pose and does not move. In some embodiments, the robotic arm 101 may also operate in various additional modes that may be combinations of the modes described above. For example, the robotic arm 101 may operate in a hybrid mode in which the robotic arm 101 (or a portion thereof) may be moved by hand guiding for certain movements of the arm (e.g., along certain directions or orientations) but may be rigid (e.g., braked) and/or provide increased resistance to other movements of the arm.

The various operating modes of the robotic arm 101 may aid in the performance of a surgical procedure, such as a minimally-invasive spinal surgical procedure or various other types of orthopedic, neurological, cardiothoracic and general surgical procedures. For example, the surgeon may move the robotic arm 101 in hand guiding mode over the patient 200 to cause the display screen 500 to display various views or slices of the patient image volume, as discussed above with reference to FIGS. 6B and 6C. Based on the image data displayed on the display screen 500, the user may set a particular target position and/or trajectory using a voice command or another input event as described above. In some embodiments, in response to the user setting a target position or trajectory, the robotic arm 101 may be configured to hold its current pose with the tip end 607 of the end effector 102 pointing along the pre-determined trajectory to the target position within the patient's body. Alternately, the target position and/or trajectory may be defined using another method (e.g., using a pointer device or via user interaction with a display device 121,401) and/or the target position/trajectory may be previously set and stored in a memory. In response to a user command for the robotic arm 101 to go to the target position or trajectory, the robotic arm 101 may be configured to autonomously move to a pose with the tip end 607 of the end effector pointing along the pre-determined trajectory to the target position.

In some embodiments, when the robotic arm 101 is pointed along a set trajectory to a target position, the robotic arm 101 may maintain a rigid or fixed pose to enable the surgeon to insert an instrument or tool through the cannula 609 into the body of the patient 200 along the set trajectory. Alternately or in addition, the robotic arm 101 may operate in a hybrid or compliant mode such that the robotic arm 101 may be hand guided in a limited range of motion (e.g., along the set trajectory towards or away from the patient 200) while all other motions may be braked. In some embodiments, the robotic arm 101 may be hand guided with increased resistance and/or reduced velocity around the initial set trajectory to enable the surgeon to make fine adjustments to the position and/or orientation of the trajectory. In other embodiments, the robotic arm 101 may enable a degree of compliance or movement with respect the set trajectory in response to an applied force on the arm, but may be configured to "snap back" to the initial set trajectory when the applied force is released. In further embodiments, surgeon may set a target position within the patient without specifying a particular trajectory for reaching the target, and the robotic arm 101 may enable hand guiding over a limited range of motion such that the tip end 607 of the end effector 102 is always pointed along a trajectory that intersects with the set target position in the patient's body. In this way, the surgeon may be able to identify an optimal pathway through the patient to reach the target position. In still further embodiments, the robotic arm 101 may enable hand guiding of at least a portion of the robotic arm over at least a limited range of motion while the robotic control system 405 may control the robotic arm 101 to make compensating movements (e.g., based on the inverse kinematics of the robotic arm 101) to maintain the tip end 607 of the end effector 102 along the set trajectory relative to the patient. For example, this may enable the surgeon to move a portion of the robotic arm 101 out of his or her way while maintaining the end effector 102 in a fixed position and/or orientation relative to the patient 200.

The target positions and/or trajectories within the patient 200 may be defined in the common coordinate system, which as noted above, may be fixed with respect to the marker device 115 (i.e., patient reference arc) that is rigidly secured to a nearby anatomic feature (e.g., a bony structure). The motion tracking system 105 may detect any movement of the patient 200 and the robotic control system 405 may control the robotic arm 101 to compensate for any detected patient movement and maintain the tip end 607 of the end effector 102 pointed along the set trajectory in the common coordinate system. Further, when the robotic arm 101 is instructed to move to or return to a particular trajectory which may have been previously set while the patient 200 is in an initial position, the robotic arm 101 may move or return to that same trajectory with respect to surgically relevant portion of the patient's anatomy, even if the patient 200 has been subsequently moved from the initial position.

Figure 7A:
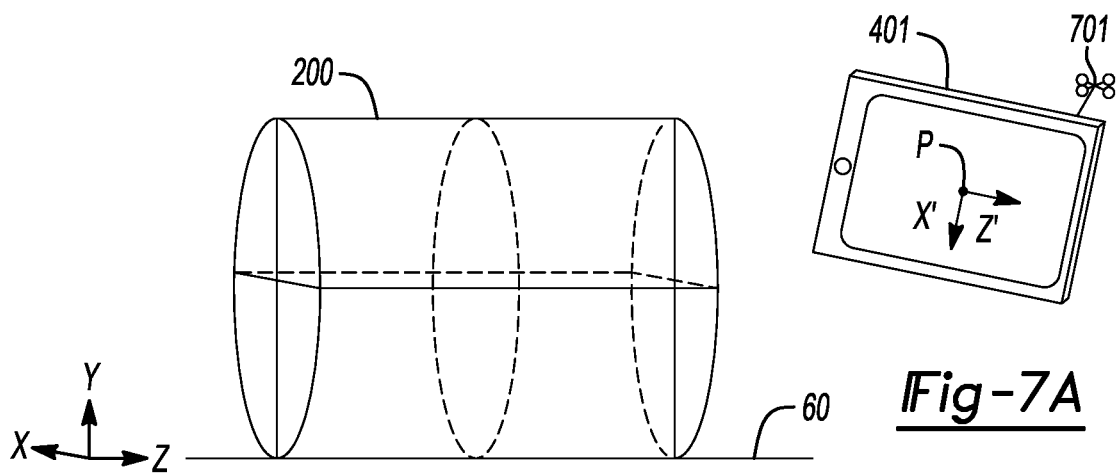
FIGS. 7A-7F schematically illustrate methods of displaying patient images in an image-guided surgery system based on a detected position and/or orientation of a handheld display device according to an embodiment.
Figure 7B:
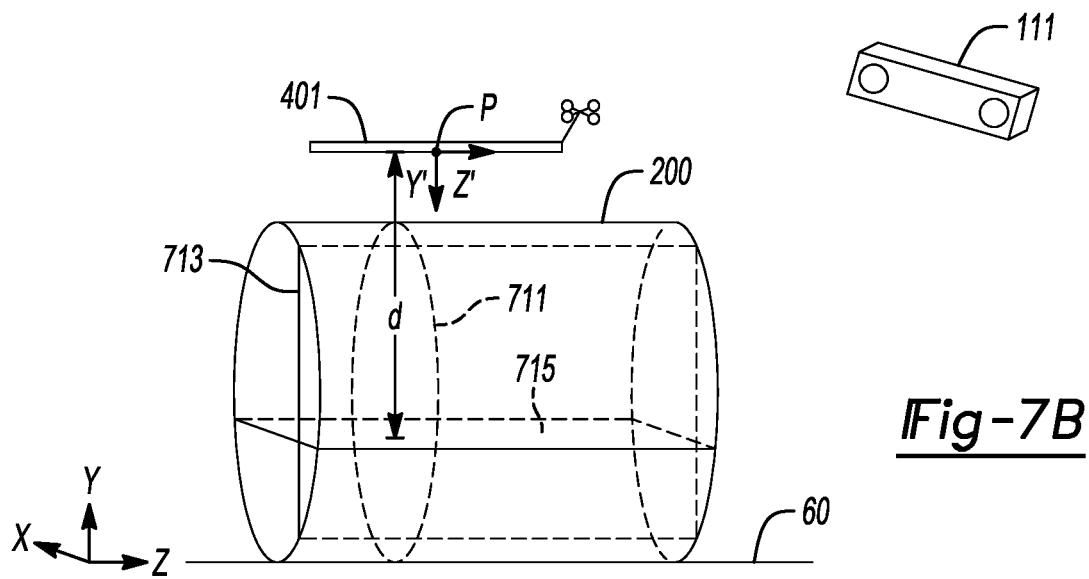

In further embodiments, at least a portion of the image data displayed on the display device 121 and/or 401 may be modified in response to a change in at least one of the position and orientation of a display device 401 with respect to the patient 200. In embodiments, the motion tracking system 105 may track the position and/or orientation of a display device. The display device 401 may be a handheld display device as described above. The handheld display device 401 may have one or more marker devices 701 fixed thereto, as schematically illustrated in FIG. 7A, which may enable the motion tracking system 105 to track the position and/or orientation of the handheld display device 401 when it is within range of the motion tracking system 105 (e.g., within the field of view of an optical sensing device 111, as shown in FIG. 7B). The one or more marker devices 701 may be in a known fixed geometric relationship with a particular point, P, on the handheld display device 401. The particular point, P, may define a coordinate system of the handheld display device 401. The point, P, may be at any arbitrary location on the handheld display device 401, such as at the center of the device 401, along an edge or midline of the device 401, or at a corner of the device 401. In embodiments, the coordinate system of the handheld display device 401 may include two mutually perpendicular axes (e.g., z' and x' axes) that extend parallel to the length and width dimensions of the device 401 and a third axis (e.g., y' axis) that extends normal to a major surface of the device 401.

In embodiments, the motion tracking system 105 may determine the location of at least a portion the handheld display device 401, such as the location of a particular point, P, on the device 401, within the patient coordinate system. The display screen 500 of the display device 401 may display different portions of the patient image dataset (e.g., a three-dimensional tomographic reconstruction) based on the detected position of the at least a portion of the handheld display device 401. In embodiments, the display screen 500 may begin displaying patient data based on the detected position of the handheld display device 401 when the device 401 is moved into a particular area, such as over the patient 200 or within a predetermined proximity to the patient surgical site. In embodiments, the display screen 500 may display patient data based on the detected position of the handheld display device 401 whenever the device 401 is within range (e.g., within the field of view) of the motion tracking system 105. In embodiments, the detected position and/or orientation of the handheld display device 401 may also determine, at least in part, the patient images shown on one or more additional display devices, such as a stationary monitor 121 as shown in FIG. 1. The one or more additional display devices 121 may mirror the display of patient images shown on the handheld display device 401.

In the embodiment of FIG. 7B, the display screen 500 may depict a two dimensional axial slice 711 of the image dataset that corresponds to the axial position of a portion the handheld display device 401 (e.g., point P) with respect to the patient 200. As the handheld display device 401 is moved with respect to the patient 200 (e.g., up and down the length of the patient in the z-axis direction), the display screen 500 may be updated to show the axial slice(s) 711 corresponding to the current position of the handheld display device 401 with respect to the patient 200.

The display screen 500 may also depict a two-dimensional sagittal slice 713 of the image dataset that corresponds to the sagittal position of a portion the handheld display device 401 (e.g., point P) with respect to the patient 200. As the handheld display device 401 is moved with respect to the patient 200 (e.g., side-to-side along the width of the patient in the x-axis direction), the display screen 500 may be updated to show the sagittal slice(s) 713 corresponding to the current position of the handheld display device 401 with respect to the patient 200.

The display screen 500 may also depict a two-dimensional coronal slice 715 of the image dataset based on the position of a portion the handheld display device 401 (e.g., point P) with respect to the patient 200. In one embodiment, the display screen 500 may depict a coronal slice 715 of the image dataset that is offset from the position of the portion of the handheld display device 401 (i.e., point P) by a pre-determined distance, d. The off-set distance, d, may be a user-adjustable parameter. As the handheld display device 401 is moved with respect to the patient 200 (e.g., towards or away from the patient along the y-axis direction), the display screen 500 may be updated to show the coronal slice(s) corresponding to the current position of the handheld display device 401 offset by the pre-determined distance, d.

The display screen 500 may also depict a three-dimensional volume rendering illustrating a "virtual" view of anatomic feature(s) (e.g., bony structures or other discrete internal anatomic features) as viewed from the current position and/or orientation of the handheld display device 401 (i.e., point P), where the "virtual" view may be updated based on the movement of the handheld display device 401.

Figure 7C:
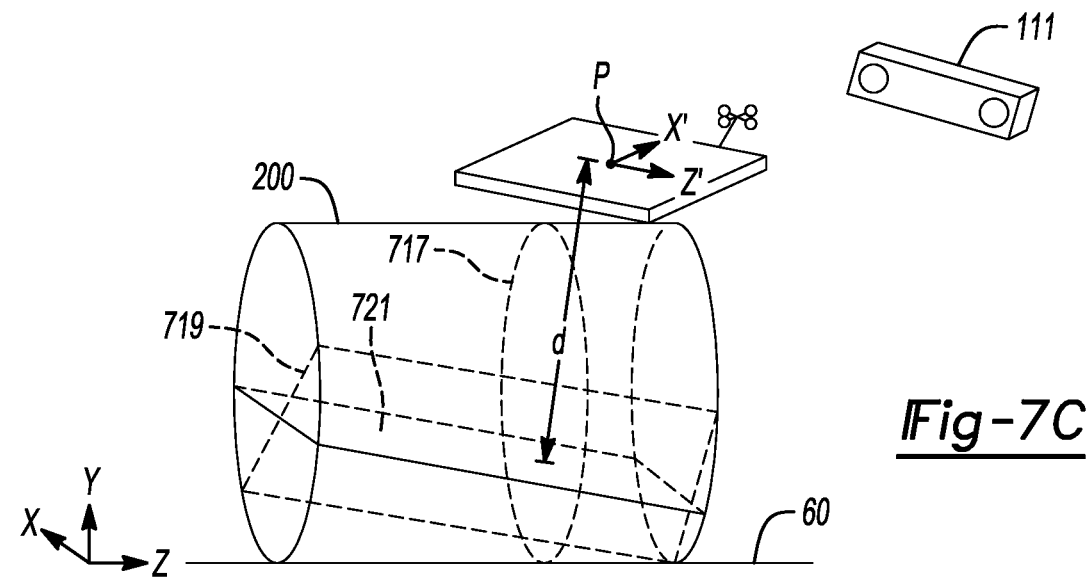

In further embodiments, the display screen 500 may display oblique two-dimensional slices of the patient image dataset (e.g., a three-dimensional tomographic reconstruction) based on the detected position and orientation of the handheld display device 401. This is schematically illustrated by FIG. 7C. In various embodiments, the display screen 500 may display two-dimensional slices (e.g., axial, sagittal and/or coronal slices) through the patient image dataset based on the position and orientation of the display 401 coordinate system with respect to the patient coordinate system. In other words, the oblique "axial" slice may be a cross-section of the patient image dataset taken in the x'-y' plane 717 of the display 401 coordinate system, the oblique "sagittal" slice may be a cross-section of the patient image dataset taken in the y'-z' plane 719 of the display 401 coordinate system, and the oblique "coronal" slice may be a cross-section of the patient image dataset in a plane that is parallel to the x'-z' plane 721 of the display 401 coordinate system and offset along the y'-axis direction by the pre-determined offset distance, d.

In various embodiments, the user (e.g., surgeon) may move the handheld display device 401 over and around the patient surgical site to provide a "virtual window" into the patient's anatomy. The user may manually hold and move the handheld display device 401 over the patient 200 and/or the handheld display device 401 may be mounted to a movable arm that may be positioned over the patient 200. The movable arm may be manually moveable and/or may be a robotic arm. In embodiments, the intersection of the three image planes (i.e., axial, sagittal and coronal) shown on the display panel 500 of the handheld display device 401 may coincide with a target position within the patient's body. Thus, the user may use the handheld display device 401 as a "virtual cutting tool" to move through the various slices/views of the patient image volume and to identify and select a target region for a surgical intervention. The user may manipulate the handheld display device 401 to display multiple trajectories or paths extending from the patient's skin surface through the patient's anatomy to the target position. The user may define one or more trajectories as discussed above via a direct user interaction with the display device 401 (e.g., via a touchscreen or stylus entry on the device 401) and/or via voice command or any of the techniques discussed above.

A handheld display device 401 (e.g., a tablet, smartphone, etc.) may include a camera (e.g., a digital camera) for obtaining photographs and/or video images. The camera may be rear-facing (i.e., on the opposite side of the device 401 from the display screen 500). The display device 401 may enable images obtained from the camera, including real-time video images, to be shown on the display screen 500 of the device. In some embodiments, the display screen 500 may display at least a portion of the patient image dataset (e.g., a three-dimensional tomographic reconstruction of a patient's anatomy) overlaying a real-time video image of the patient. In various embodiments, the display screen 500 may display different portions of the patient image dataset based on the camera's location with respect to the body of the patient.

Figure 7D:
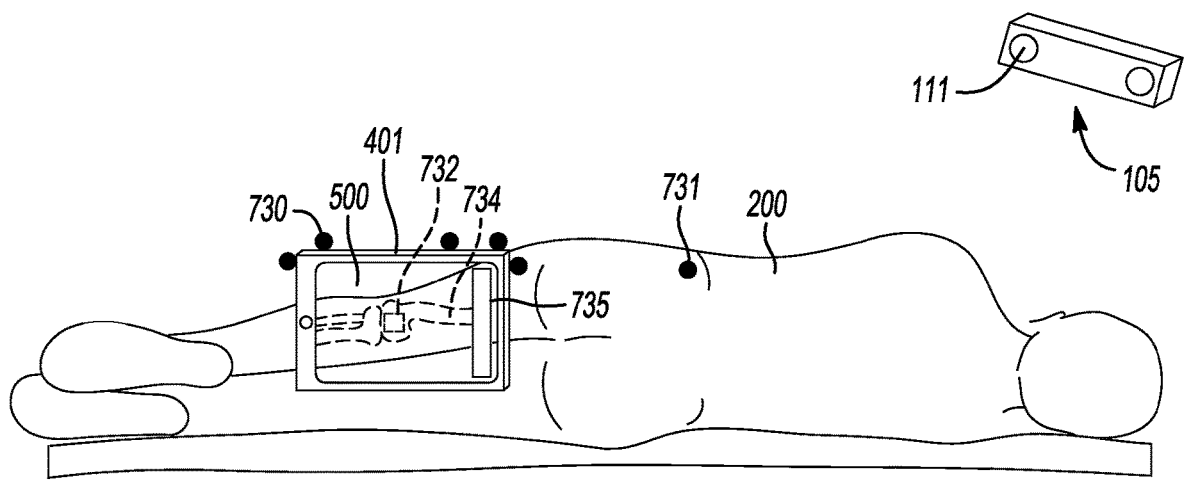
Figure 7E:
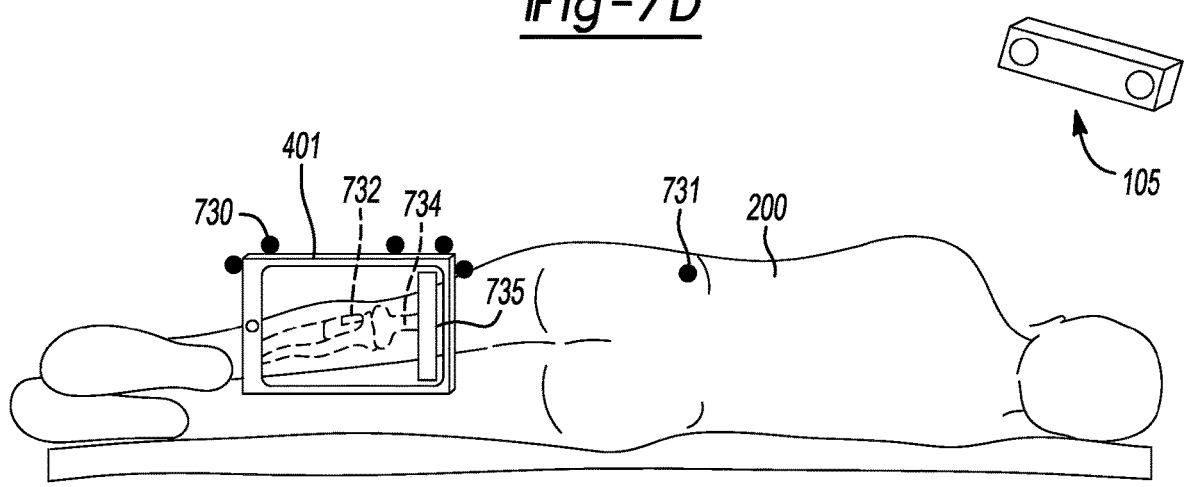

FIGS. 7D-7E illustrate a handheld display device 401 having a rear-facing camera (schematically illustrated by 732) that is configured to images of a patient 200 obtained by the camera 732 on a display screen 500. In this embodiment, the display device 401 includes a plurality of markers 730 (e.g., reflective spheres) that may be attached to the display device 401 using a suitable attachment mechanism. The markers 730 may enable the display device 401 to be tracked by a motion tracking system 105 as described above. In this embodiment, the markers 730 are attached along a first edge of the display device 401 so that user (not shown) may securely grasp and hold the display device 401 by or between the other edges without occluding the markers 730 from the field of view of the optical sensor device 111 of the motion tracking system 105.

The motion tracking system 105 may track the position and orientation of the handheld display device 401. One or more additional markers 731 on the patient 200 may enable the position and orientation of the display device 401 to be determined relative to the patient 200. The patient marker(s) 731 may further enable registration of patient images (e.g., CT and/or MRI data) in a common coordinate system, as discussed above. In embodiments, the images from the camera 732 (e.g., real-time video images) may be overlaid with a three-dimensional volume rendering illustrating a "virtual" view of anatomic feature(s) (e.g., bony structures or other discrete internal anatomic features) as viewed from the current position and/or orientation of the handheld display device 401. A calibration process, which may be performed by a processor on the display device 401 and/or on another device (e.g., computer 113 shown in FIG. 1), may be used to match the three-dimensional volume rendering to the field of view of the camera 732 so that the images of the patient 200 taken by the camera may be augmented by a rendering of the underlying anatomical features as viewed from the same camera position.

This is illustrated in FIG. 7D, which shows the handheld display device 401 positioned such that a portion of the patient 200 is within the field of view of the camera 732. The display screen 500 shows a video image of the patient 200 that is overlaid by a three-dimensional volume rendering 734 of the corresponding internal anatomy (shown in phantom). The volume rendering may be updated as the handheld display device 401 is moved with respect to the patient 200 so as to depict the corresponding internal anatomy as viewed from the updated camera position. This is illustrated in FIG. 7E, which shows the updated three-dimensional volume rendering 735 as the handheld display device 401 is moved along the length of the patient 200. In embodiments, the augmented images shown on the display screen 500 of the handheld display device 401 may be mirrored on one or more additional display screens, such as a monitor display 121 as shown in FIG. 1.

In some embodiments, the user may be able to make the superimposed image data (e.g., 3D volume rendering 734) more or less transparent relative to the camera images (e.g., real-time video images) shown on the display screen 500. A slider 735 or similar graphical interface element on the display screen 500 (e.g., a touchscreen display) may be used to adjust the relative transparency of the 3D volume rendering relative to the camera images, as shown in FIG. 7F.

Figure 7F:
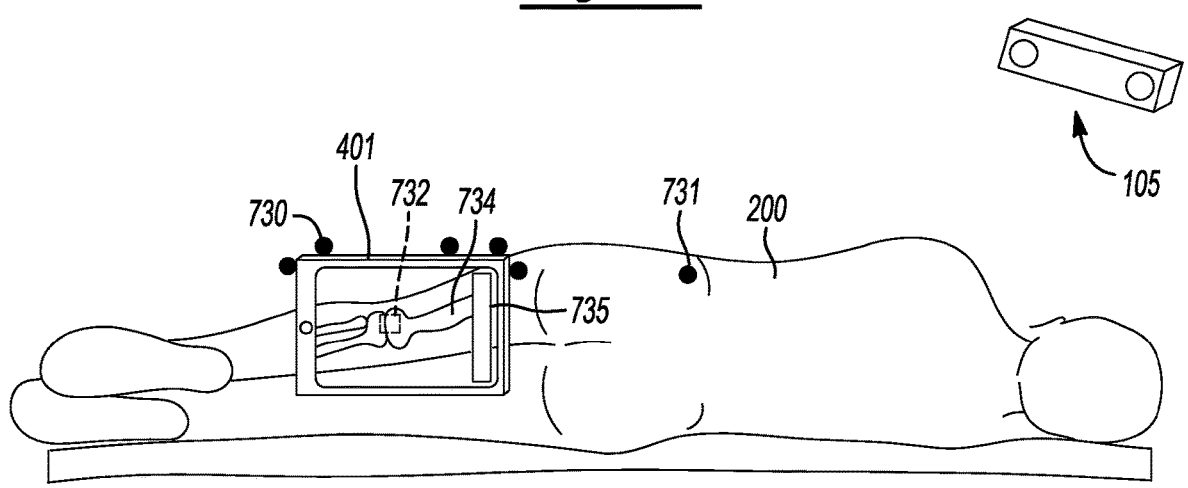

A handheld display device 401 such as shown in FIGS. 7D-7F may be used before, during and/or after a surgical procedure to provide the surgeon with a "virtual" window into the patient's anatomy, as described above. Alternately or in addition, a handheld device 401 such as shown in FIGS. 7D-7F may be used for diagnostic purposes by providing a dynamic tool for looking around the patient and into the underlying anatomy. The handheld device 401 may be used as an explanatory aid for patients. In some embodiments, the patient marker 731 may be fixed over the skin surface of the patient 200 (e.g., via an adhesive or other means) and may include an x-ray opaque beebee or other element identifiable in the image data to enable registration of the image data to the coordinate system of the motion tracking system 105.

A handheld display device 401 as described above may be located within or moved into the surgical sterile field. Since typical handheld electronic devices, such as tablet computers, are not sterile or sterilizable, the handheld display device 401 may be placed within a sterilized enclosure, such as a sterile drape or bag. However, a typical sterile bag or covering used in a surgical environment may negatively impact the functionality of a handheld computing device, such as by obscuring the view of the display screen, interfering with user input components, such as a touchscreen user interface, and/or interfering with the motion tracking of the device. A sterile bag or covering may also make the device more difficult to hold and manipulate by a user.

FIGS. 8A-8E illustrate a sterile case 800 for a handheld display device 401 according to an embodiment. FIG. 8A is a front elevation view of the case 800 and FIG. 8B is a rear elevation view of the case 800. As shown in the perspective view of FIG. 8C, the case 800 may have a clamshell design, with a first portion 801 connected to a second portion 803 by a hinge portion 805. The first portion 801 and the second portion 803 may be folded over on the hinge portion 805 to enclose a handheld display device 401 between the first and second portions 801, 803. When the first portion 801 and the second portion 803 are folded together, the interfacing surfaces of the first and second portions 801, 803 may define an interior housing 807 of the case 800. In embodiments, the interior housing 807 may be dimensioned to correspond to the dimensions of a handheld display device 401 received therein. An outer surface of the first portion 801 may define the front surface 802 of the case 800 and an outer surface of the second portion 803 may define the rear surface 804 of the case 800.

The case 800 may be made from a sterile, transparent material, such as a plastic, and may be relatively low-cost. In embodiments, the case 800 may be a single-use disposable component. In other embodiments, the case 800 may be re-sterilizable (e.g., autoclavable), and may be a reusable component. In embodiments, the case may be custom designed for use with a particular handheld display device (e.g., tablet computer, pendant controller, etc.).

In various embodiments, the case 800 may have an integrated marker device to enable the case 800 and handheld display device 401 to be tracked by a motion tracking system, as described above. In one embodiment, a plurality of markers 809 (e.g., IR reflective spheres) may be mounted to the case 800. In embodiments, the markers 809 may be enclosed within the case 800 and may form an array pattern that may be tracked by a motion tracking system. Alternately or in addition, a separate marker array pattern may be attached to the outside of the case 800. As shown in FIG. 8C, the case 800 may have a plurality of internal pockets 811 that may be sized and shaped to receive spherical reflective markers 809. The pockets 811 may be disposed around an outer periphery of the case 800, and may have an asymmetric pattern such that the marker array may have a different geometry when viewed from the front 802 and back 804 of the case 800. Instead of reflective spheres, the markers 809 can also be flat (e.g., disk-shaped) reflective markers that may be located within the case 800 or attached to an outer surface of the case 800.

The case 800 may have a sufficiently rigid construction to prevent the markers 809 from moving relative to one another and relative to the handheld display device 401. The front surface 802 of the case may include a substantially flat window region 812 that encompasses the display screen of the handheld display device 401. The window region 812 may be sufficiently rigid to inhibit distortion when viewing display screen through the window region 812, and may relatively thin to enable touchscreen control of the display device through the case 800. In some embodiments, the window region 812 may have an anti-glare and/or anti-reflective coating to minimize the impact of external reflections, such as from overhead surgical lights. In some embodiments, when the case 800 and display device 401 are determined to be in proximity to the patient surgical site by the motion tracking system 105, a signal may be sent to a controller for controlling a light source (e.g., overhead surgical lights) to cause the light source to modify the room lighting (e.g., dimming or changing the focus of the lights) to enable the display to be more clearly viewed.

The first and second portions 801, 803 of the case 800 may have mating portions 813 (e.g., projections, detents, etc.) that may fit together to hold the case 800 in a closed position. The case 800 may also include an additional locking mechanism 815 that may be secured over the case 800 to hold the case 800 in a closed position. As shown in FIGS. 8D and 8E, the locking mechanism 815 may include a slider 816 that may be inserted over and slid along a track 818 on the periphery of the case 800 to ensure that the case 800 does not accidentally open during a surgical procedure. In some embodiments, the locking mechanism 815 may also enable the case 800 to be mounted to a separate support element. For example, as shown in FIGS. 8D and 8E, the upper portion of the slider 816 may include a projection 819 that may function as a latch portion (e.g., a strike plate) when the projection 819 is inserted into a releasable latching member 821 on the support element. The releasable latching member 821 may function similarly to a seatbelt belt buckle in a vehicle. The support element may include one or more features 823 that may mate with corresponding features 826 (see FIG. 8B) on the rear surface 804 of the case 800. For example, the support element may include a loop member 823 that may fit within an arc-shaped detent 826 formed in the rear surface 804 of the case 800. Other mechanisms for mounting the case 800 to a support may be utilized. The case 800 containing the handheld display device 400 may be easily removable from the support element by a user, and may be easily re-attached to the support element. In embodiments, the rear surface 804 of the case 800 may have handles 827, which may be molded features in the rear surface 804, to facilitate easy grasping and manipulation of the case 800 and display device 401 by the user.

Figure 8F:
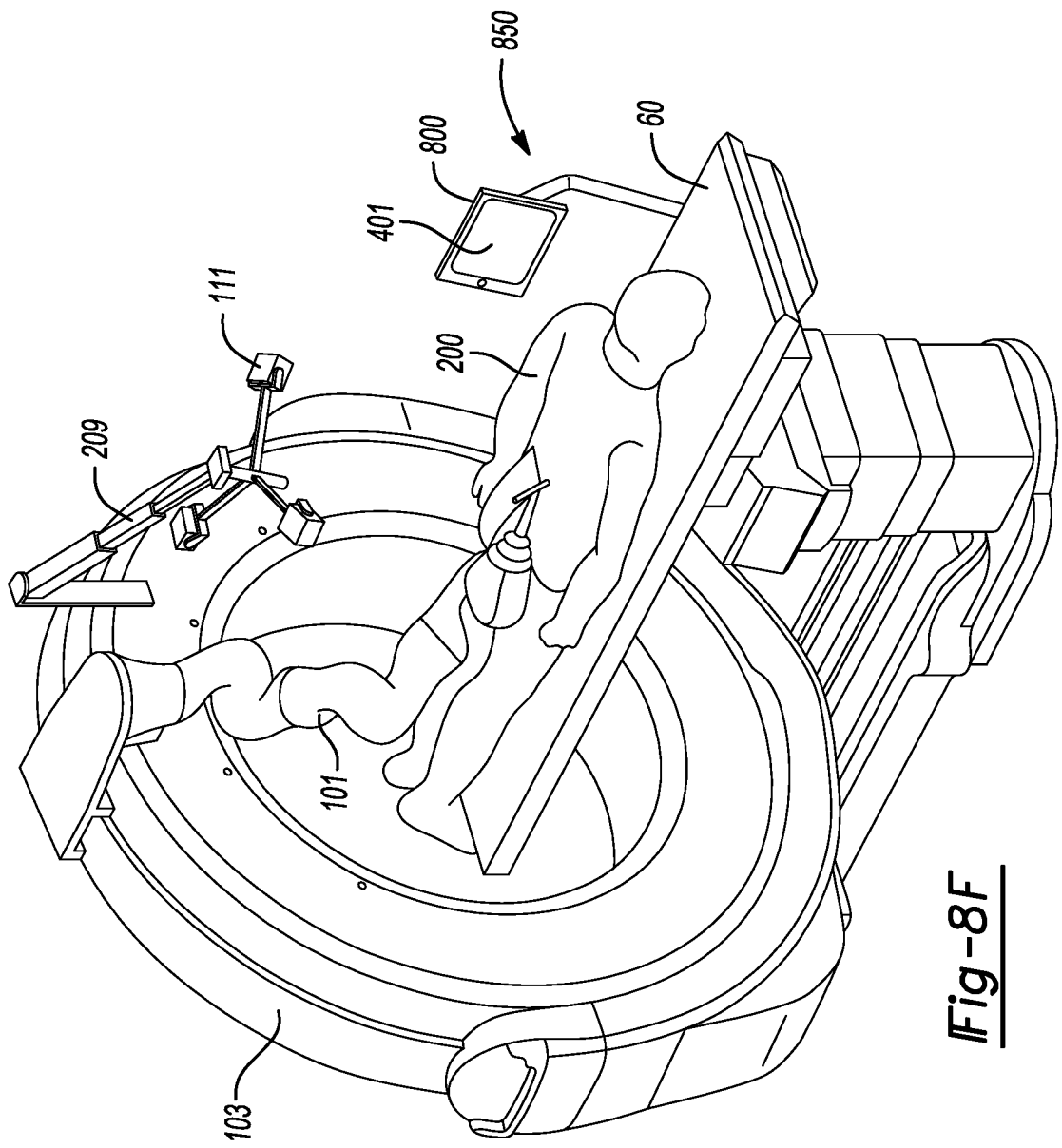

FIG. 8F illustrates a handheld display 401 within a sterile case 800 that is mounted to an adjustable support 850 (e.g., a gooseneck, balanced-arm or pivoting-arm support stand). The support 850 for the handheld display device 401 may be attached to the patient table 60, such as by mounting the support 901 to surgical side rails. The support 850 may be attached to any other component, such as a separate cart, the imaging device 103, a robotic arm 101, or may be suspended from an overhead structure (e.g., overhead lights). In one embodiment, one or more handheld display devices 401 may be suspended from an arm 209 extending above the patient 200 surgical area, which may also support an optical sensor device 111 for the motion tracking system.

Figure 9:
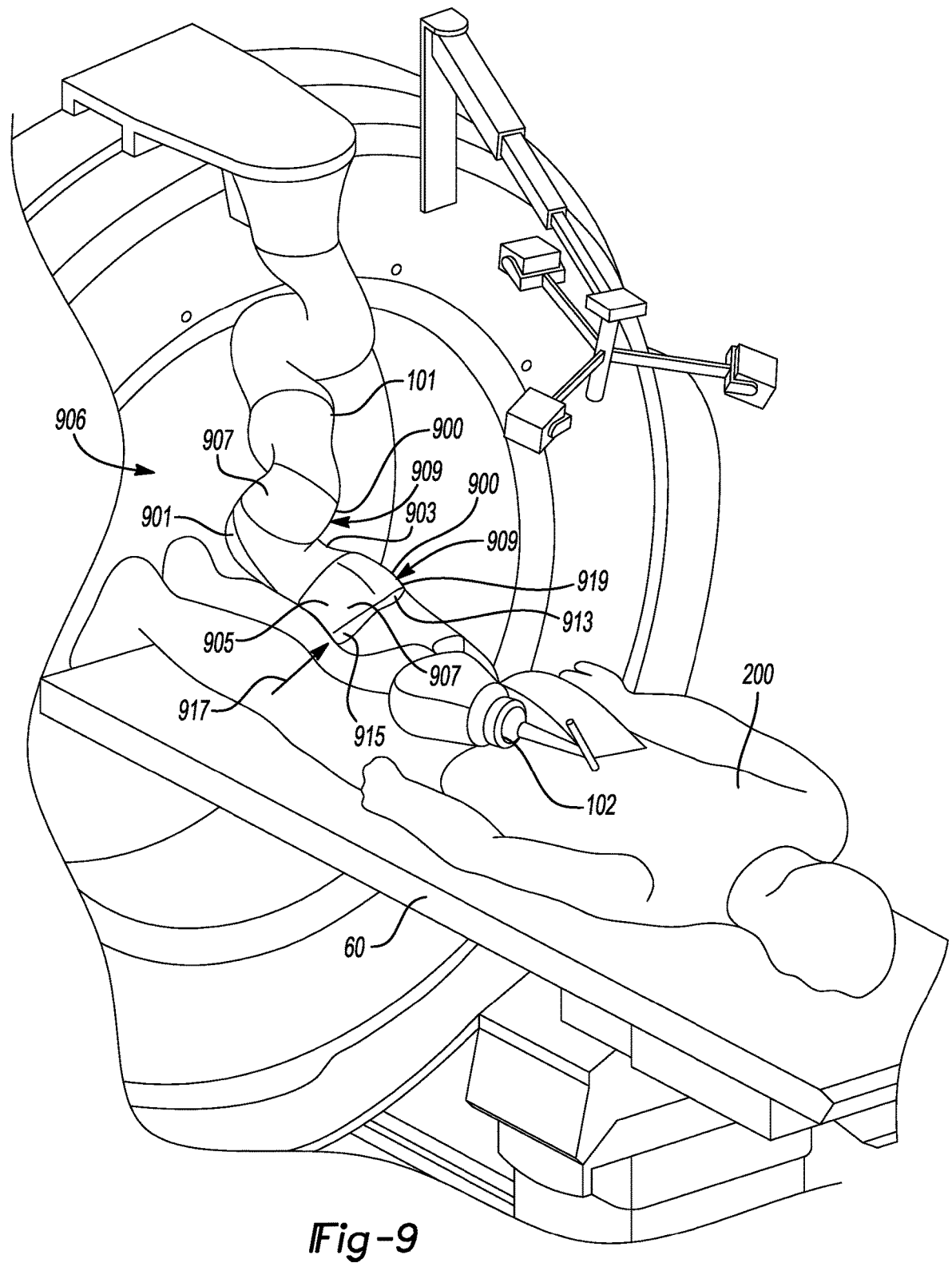
FIG. 9 illustrates a robotic arm having a display device on the robotic arm according to an embodiment.

In some embodiments, at least one display device 900 may be provided on a robotic arm 101, as is illustrated in FIG. 9. The at least one display device 900 may optionally display status and system information related to the operation of robotic arm 101 and may also be used for displaying patient information, including imaging data obtained using an imaging device 103, as well as surgical navigation data from an image-guided surgery system 400. The image data may include 2D slices of a three dimensional image dataset (e.g., a tomographic reconstruction) and/or a 3D volume rendering of all or a portion of the image dataset. The images displayed on display device 900 may include all or a portion of the images that may be displayed on display devices 119 and/or 401, as described above. Thus, the at least one display device 900 on the robotic arm 101 may be a mirror of display device 119 and/or 401. The images may be reformatted to fit within the display device 900. In other embodiments, the images displayed on display device 900 may be different from those shown on a separate stationary display (e.g., monitor 119) or a handheld display device 401. In embodiments, multiple display devices 900 may be provided on different sections of a robotic arm 101. Each display device may display the same or different images (e.g., each display 900 may display a different 2D slice of a three-dimensional image dataset). The display(s) 900 may further include user interface components (e.g., touchscreen interface, buttons, etc.) that may enable a user to control what is shown on the display device 900 and/or control a function or operation of the robotic arm 101.

The robotic arm 101 may be an articulated robot having a plurality of rotary joints 901 with linkage members 903 between the joints 901. In many cases, the linkage members 903 may have a generally curvilinear or cylindrical shape around their outer periphery (i.e., circumference). In embodiments, the at least one display device 900 may be located on one or more linkage members 903 of the robotic arm 101. In some embodiments, a display device 900 may include a contoured viewing surface 905 that may extend around an outer periphery of the linkage member 903. In particular, the contoured viewing surface 905 may extend around at least 50% of the outer periphery of the linkage member 903, such as between 50-100% (e.g., 60-90%) of the outer periphery of the linkage member 903.

In embodiments, the display device 900 may include multiple flat-panel display tiles disposed around the periphery of the linkage member 903 and angled to approximate the contour of the outer surface of the linkage member 903. Individual tiles may be controlled to display a portion of a continuous image extending over multiple tiles, with narrow mullions (e.g., <1 mm) between adjacent tiles. Each tile may have a dimension that is less than 2 inches (e.g., approximately 1 inch) in the direction extending around the periphery of the linkage member 903. The display device 900 may utilize any suitable display technology, such as an LCD display, an LED display, an OLED display or a front or rear projection display.

In some embodiments, all or a portion of the display device 900 may be formed on a curved or flexible substrate that follows the contour of the outer surface of the linkage portion 903. The display device 900 may be, for example, an organic light-emitting diode (OLED) display on a curved or flexible substrate. In embodiments, the display device 900 may comprise an active matrix of organic thin-film transistors (OTFTs) on a flexible substrate coupled to a liquid crystal display (LCD) medium, such as disclosed in WO 2015/177539 by FlexEnable Ltd., which is incorporated by reference herein. In embodiments, the display device 900 may comprise a reflective display having an electrophoretic display medium (e.g., electronic ink) on a curved or flexible substrate.

In some embodiments, one or more connections for providing power to and exchanging data with the display device 900 may be located on the outer surface of the linkage member 903. The display device 900 may be snapped over or adhered to the linkage member (e.g., using an adhesive and/or mechanical fasteners) and plugged into a connector (e.g., USB port) on the robotic arm 101. Alternately, the display device 900 may be permanently mounted to or integrally formed with the robotic arm 101. Wire connections to the display device 900 for power and data may extend through the interior of the robotic arm 101. In some embodiments, the display device 900 may include transceiver circuitry to enable wireless communication with a separate computer device (e.g., image guided surgery system 400). The display device 900 may have an internal battery power source, and a separate power connection may not be needed.

In embodiments, a surgical drape (not shown for clarity) may be provided over the robotic arm 101 to provide a sterile barrier between the robotic arm 101 and the surgical area. The display device 900 mounted to the robotic arm 101 may be viewable through the drape, which may be made of a transparent material. In some embodiments, in order to improve viewability of the display device 900, the drape may be adhered to or otherwise held flat against the viewing surface of the display device 900. The drape may be adhered to the viewing surface of the display device 900 via an adhesive or mechanical fasteners, heat shrinking the drape, or using suction forces. In some embodiments, the drape may be held against the display device 900 using electroadhesion forces. For example, electrodes embedded in a dielectric material on the robotic arm 101 and/or the display device 900 may be used to prehend the drape against the viewing surface (e.g., similar to an electrostatic chuck used in semiconductor wafer processing).

In some embodiments, one or more display devices 900 may be located on the surgical drape and may be attached to the robotic arm 101 when the drape is placed over the robotic arm 101. The drape and the one or more display devices 900 located thereon may be single-use disposable components.

As noted above, linkage members 903 of the robotic arm 101 may be connected to one or more rotational joints 901. During operation of the robotic arm, 101, each linkage member 903 and any display device(s) 900 mounted thereon may thus have rotational freedom in one or more directions. In some cases, this may interfere with the viewing of the display device 900, such as where the viewing surface is rotated to a different orientation with respect to the viewer such that the viewing surface is no longer visible to the viewer. In embodiments, a controller operatively coupled to the display device 900 may be configured to detect a rotational motion of the display device 900 with respect to a viewing position 905 and may modify at least one image shown on the display device 900 in response to the detected rotational motion. The controller may modify the at least one image shown on the display device 900 such that it remains visible to a viewer in the viewing position 906 as the portion of the robotic arm 101 on which the display device 900 rotates with respect to the viewing position 906. In some embodiments, the viewing position 906 may be a location above and proximate to the surgical area (e.g., within 5 meters, such as within 2 meters, e.g., within 1 meter, of the surgical area), where a user (e.g., a surgeon) may view the display device 900 during a surgical procedure. The viewing position 906 may optionally be pre-set by the user (e.g., to accommodate the user's height and/or where the user will be situated during the procedure, such as on a particular side of the surgical table 60), such as by manually adjusting the display settings until the information of interest may be clearly viewed. The display device 900 may display the at least one image on a first portion 907 of the display device 900 such that the at least one image may be clearly seen from the viewing position 905. For example, the first portion 907 may be a segment of the display device around the periphery of the linkage member 903 that faces upwards towards the user. A second portion 909 of the display device 900 that is not clearly viewable from the viewing position 905 (e.g., a segment of the display device 900 that faces downwards and/or away from the user) may not display any images.

In embodiments, the controller of the display device 900 may detect the orientation of display device 900 based on the current joint parameters of the robotic arm 101 and the known gravity vector 911 at the base 912 of the arm 101 (see FIG. 8F). At least one image may be displayed based on the detected orientation of the display device 900. For example, for a display device 900 that extends around all or substantially the entire periphery of the linkage member 903 of the robotic arm 101, the display device 900 may display at least one image on a portion of the linkage member 903 facing opposite the gravity vector 911 (i.e., such that the image may be seen from the viewing position 905). In embodiments, no image may be displayed on a portion of the linkage member 903 facing in the direction of the gravity vector 911. Alternately or in addition, the orientation of the display device 900 may be determined using an inertial measurement unit (IMU) (e.g., accelerometer(s) and/or gyroscope(s)) located on the display device 900 or the robotic arm 101, or using data from the motion tracking system 105.

In embodiments, the controller may determine a rotational motion of the display device 900 relative to the viewing position 905 based on a change in the joint parameters of the robotic arm 101 and the known kinematics of the robotic arm 101. Alternately or in addition, the rotation motion of the display device 900 may be determined based on a signal from an IMU or from the motion tracking system 105. In response to a rotational motion of the display device 900, the controller may modify the at least one image shown on the display device 900 such that the one image remains visible to a viewer in the viewing position 905. For example, the at least one image may be scrolled over the surface of the display device 900 such that the at least one image continues to face the viewing position 905. In embodiments, the display device 900 may optionally also re-orient the at least one image on the display screen such that the image maintains an initial orientation with respect to the viewing position 905.

In embodiments, at least one display device on a robotic arm 101 may indicate an operational status of the robotic arm 101. For example, at least one display device on the robotic arm 101 may provide an indication of a current operating mode of the robotic arm 101, such as a handguided mode, an autonomous mode, a static (braked) mode or any other operating mode such as discussed above. The operating mode of the robotic arm 101 may be displayed on a display device 900 as described above, or may be displayed on a separate display device 913, which may be an LED light pipe extending around the robotic arm 101. The operating mode may be displayed by displaying a readily perceivable and understandable indicator, such as a color-coded indication of the current operating mode of the robotic arm 101.

In various embodiments, a plurality of display devices 900 and/or 913 may be located on multiple portions of the robotic arm 101 that are moveable relative to one another, such as on a plurality of linkage members 903. In some embodiments, the robotic arm 101 may be operated in a hybrid operating mode, such that at least one portion of the robotic arm 101 may be moved by a user in a handguiding mode while another portion of the arm may be in a braked or increased resistance mode. For example, the robotic arm 101 may be in a pose such that the end effector 102 of the arm 101 maintains a particular trajectory with respect to the patient 200. In some cases, it may be desirable for a portion of the robotic arm 101 to be moved (e.g., moved out of the way of the surgeon) while maintaining the end effector 102 in the pre-determined trajectory with respect to the patient 200. Using the known inverse kinematics of the robotic arm 101, the robotic control system may determine which portion(s) of the robotic arm 101 may be safely moved while sufficient compensating movements exist to enable the end effector 102 to maintain the pre-determined trajectory with respect to the patient 200. The plurality of display devices 900 and/or 913 may display different indicators (e.g., different colors) to indicate whether a particular portion of the arm 101 may be moved in a handguiding mode. For example, a display 900,913 on a first portion of the arm 101 (e.g., a first linkage member 903) may display a first color (e.g., green) to indicate that that portion of the arm 101 may be moved via handguiding. A display on a second portion of the arm 101 (e.g., a different linkage member) may display a second color (e.g., red) to indicate that that portion of the arm 101 may not be moved via handguiding. In some embodiments, the display 900, 913 may display an additional indicator (e.g., a yellow color) to indicate that a particular portion is about to enter a braked or locked mode, such as when the arm is moved into a configuration such the robotic arm 101 will no longer be able maintain the end effector 102 in the predetermined trajectory relative to the patient 200 and/or when a joint limit of the robotic arm 101 is about to be reached.

Alternately or in addition, a display 900, 913 on a portion of the robotic arm 101 may provide an indication of a direction in which the portion of the arm may be moved by handguiding. For example, as shown in FIG. 9, the display 913 on linkage member 903 may display an indicator (e.g., a first color) on a first portion 915 of the display 913 to indicate that the linkage member 903 may be moved (i.e., handguided) in a first direction (indicated by arrow 917). The display 913 may display a second indicator (e.g., a second color), or may display no indicator, on a second portion 919 of the display 913 to indicate that the linkage member 903 is braked in other directions. For example, the display(s) 900,913 may display a first color (e.g., green) to indicate directions) in which the robotic arm 101, or a portion 903 thereof, may be pushed in a handguiding mode. The display(s) 900, 913 may optionally display a second color (e.g., red) to indicate direction(s) in which the robotic arm 101 is braked and may not be handguided. This may be used, for example, when the robotic arm 101 is in a hybrid mode such that the robotic arm 101 may be handguided over a limited range or in limited direction(s) (e.g., along a particular trajectory with respect to the patient 200), but is otherwise braked.

Further embodiments include methods of performing image guided surgery using multiple patient reference marker devices. As discussed above, a reference marker device 115 (e.g., reference arc) may be rigidly attached to a landmark in the anatomical region of interest (e.g., clamped or otherwise attached to a bony portion of the patient's anatomy) to enable the anatomical region of interest to be continually tracked by the motion tracking system 105. During an image guided surgical procedure, the diagnostic imaging data of the relevant anatomy may be registered to a patient coordinate system based on the position and orientation of the reference marker device 115, which may be continually tracked by the motion tracking system 105. In general, the accuracy of the patient registration of the diagnostic imaging data may be greatest at portions of the anatomy closest to the attachment point of the reference marker device 115. The accuracy of the registration may decrease the further one gets from the attachment point of the reference marker device 115. This may be due to small movements of the patient's anatomy relative to the anatomical feature to which the reference marker device 115 is affixed, which may cumulatively produce larger relative displacements the further one is from the affixation point. Thus, for a complex surgical procedure requiring interventions over a large area of the patient's anatomy, such as a spinal surgery involving multiple spinal vertebral levels, a typical workflow may include performing multiple imaging scans and patient registrations, with the patient reference marker device 115 being removed and surgically reattached to different portions of the patient's anatomy prior to each successive scan and registration step. This may greatly increase the duration and complexity of the surgical procedure.

Figure 10A:
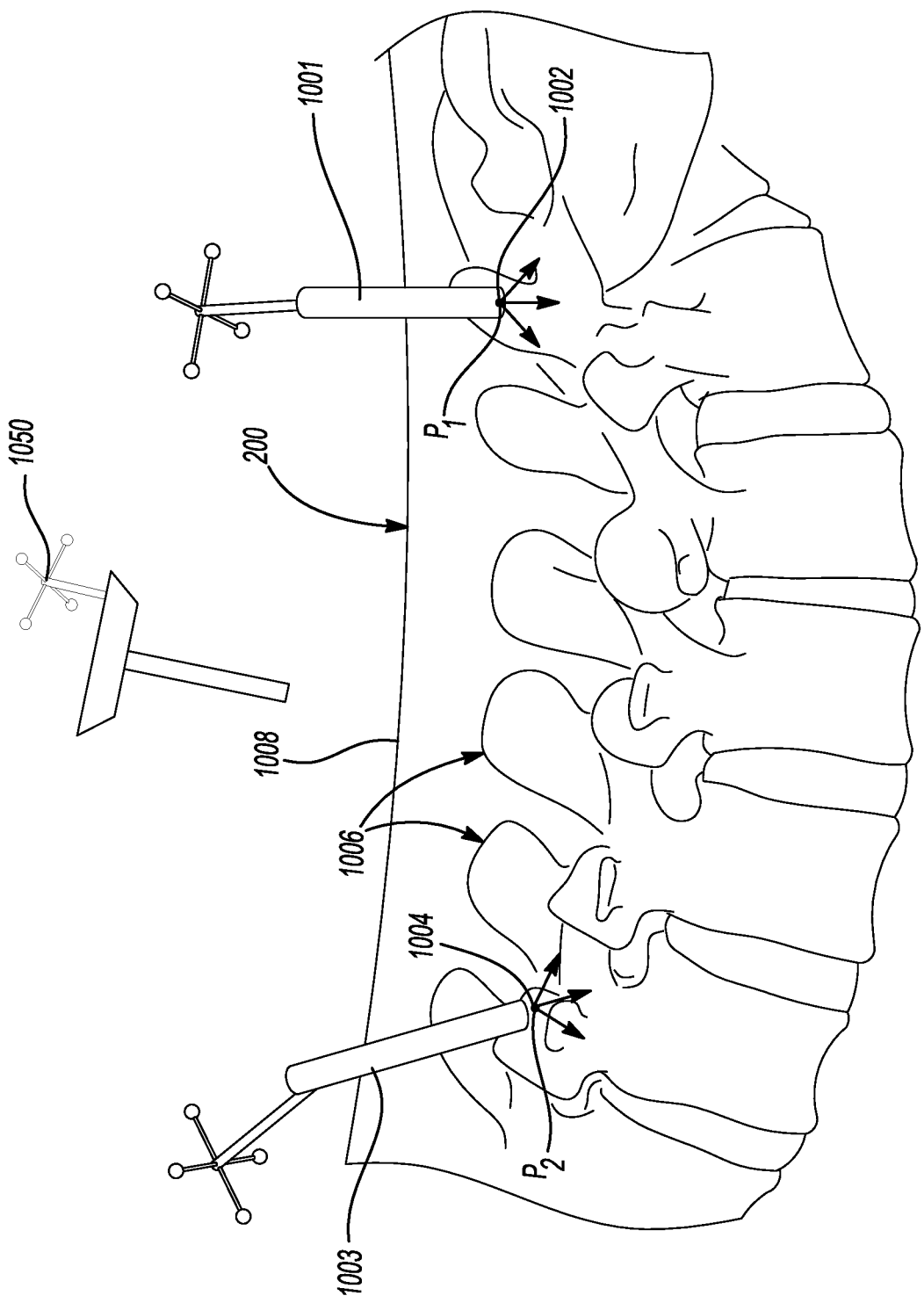
FIG. 10A is a cross-section side view of a spine of a patient having a plurality of reference marker devices attached thereto.

FIG. 10A illustrates an embodiment image-guided surgical procedure using multiple reference marker devices 1001, 1003 fixed to a patient 200. FIG. 10A schematically illustrates a side cross-section view of the patient's anatomy, and in particular a lower (lumbar) spinal region of the patient. In embodiments, a plurality of reference marker devices 1001, 1003 are attached to different positions 1002, 1004 of the patient's anatomy. Each reference marker device 1001, 1003 may be rigidly attached to a different bony structure, such as a portion of a vertebra (e.g., a spinous process 1006). The attachment positions 1002, 1004 may be separated by a distance of 2 inches or more, such as 2-5 inches, and may be separated by 4-6 inches, including about 5 inches, and in some embodiments may be separated by 6 inches or more. For a spinal surgical procedure, the attachment positions 1002, 1004 may be located on different vertebral levels of the spine, which may be separated by at least one, and preferably greater than one (e.g., 2-5) intervening vertebral levels. The different vertebral levels may be lumbar, thoracic and/or cervical vertebral levels. The attachment positions 1002, 1004 may also be located on different anatomic structures. For example, a first attachment position 1002 may be on a vertebral structure and the second attachment position 1004 may be on a different bony structure, such as the iliac crest of the pelvis. Although two reference marker devices 1001, 1003 are shown attached to the patient in FIG. 10A, it will be understood that more than two reference marker devices may be attached to different portions of the patient in various embodiments.

Each reference marker device 1001, 1003 may include an elongated member having a mechanism at one end for attaching to the patient. For example, the reference marker device 1001 may include a clamp that is configured to attach to the spinous process of a vertebra. A second end of the reference marker device 1001, 1003 may extend outside of the skin 1008 of the patient 200. An array of markers (e.g., a plurality of reflective spheres in a geometric array) may be attached to the second end of the marker device 1001, 1003 to enable the marker devices 1001, 1003 to be tracked using a motion tracking system 103.

In some embodiments, the reference marker devices 1001, 1003 may be minimally-invasive reference marker devices. An example of a minimally-invasive marker device is shown in FIG. 10B. The minimally-invasive marker device 1001 may include an elongated member (e.g., a rod) 1010 having a relatively small diameter, such as less than about 8 mm (e.g., 4-7 mm), including about 6 mm. The elongated member 1010 may be a hollow tube. In embodiments, the elongated member 1010 may be made from a material that may be visible in the image data, such as carbon fiber. In the case of x-ray CT data, the elongated member 1010 may function as a fiducial that is visible in the CT images and may be used by the surgeon to verify the registration accuracy, as discussed further below. A threaded screw 1012 may be located at one end of the elongated member 1010 for attaching to a structure in the patient's anatomy, and an array of markers 1014 may be attached to the opposite end. The elongated member 1010 may also include one or more additional anchors 1016 that may dig into the surrounding bone when the screw 1012 is screwed into the patient's bone to aid in affixing the marker device 1001 to the patient. The threaded screw may have a maximum diameter that is approximately equal to or less than the diameter of the rod 1010. In embodiments, a screw driver may be inserted through the hollow interior of the elongated member 1010 to engage with the threaded screw 1012 to affix the marker device 1001 to a portion of the patient's anatomy.

In various embodiments of a minimally-invasive marker device, the portion of the reference marker device that is inserted into the patient may have a smaller profile than conventional reference marker devices, which may typically include clamping members for affixing to a bony structure. In embodiments, a minimally-invasive reference marker device 1001, 1003 may be inserted through a small opening or incision in the patient's skin and the threaded screw may be screwed directly into the patient's bone. Attaching a plurality (e.g., 2, 3, 4 or more) of such marker devices around the surgical area may provide redundancy such that if one marker device is not rigidly secured or becomes loose, any loss in the accuracy of the surgical navigation may be compensated for by one or more additional marker devices. The marker devices 1001, 1003 may also be used to verify the accuracy of the patient registration. The registration may become inaccurate, for example, if a marker device 1001, 1003 becomes loose or is accidentally bumped causing it to change its position relative to the patient during a surgical procedure. In embodiments, the surgeon may utilize one or more marker devices 1001, 1003 as a fiducial to periodically check the registration accuracy during a surgical procedure. This may include, for example, using an instrument (e.g., a pointer 1050 or stylus, see FIG. 10A) that is tracked by the motion tracking system 105 to verify that the actual location of the marker device 1001, 1003 at a given time corresponds to the location of the marker device 1001, 1003 that is visible in the patient image(s). This may include, for example, using a pointer 1050 to touch or trace along a portion of the marker device 1001, 1003 that projects outside of the patient's skin and/or positioning the pointer 1050 along the trajectory defined by the elongated member 1010 of the marker device 1001, 1003 to ensure that the marker device 1001, 1003 has not moved relative to the patient subsequent to the initial registration. A discrepancy between the location of the marker device 1001, 1003 measured using the pointer 1050 and the location of the marker device 1001, 1003 visible in the patient image(s) may indicate that the patient registration is no longer accurate.

In embodiments, a minimally-invasive reference marker device may require an opening through the patient's skin and muscle of less than 10 mm in width for insertion and fixation of the marker device to bone, compared to conventional reference marker devices, which may require openings that are greater than 12 mm in width to enable the marker device to be inserted into and clamped onto the bone of the patient. In some embodiments, a minimally-invasive reference marker device may include a sharp point or blade on the tip end of the device such that the marker device itself may be used to perform the incision through the patient's skin. In some embodiments, the minimally-invasive marker devices may be single-use disposable components.

FIG. 11A is a process flow diagram illustrating an embodiment method 1100 for performing image-guided surgery using multiple reference marker devices fixed to a patient. The method 1100 may be performed using an image-guided surgery system, such as system 400 described above with reference to FIG. 4. In embodiments, the multiple reference marker devices may be reference marker devices 1001, 1003 as shown in FIG. 10A and may be minimally-invasive reference marker devices as shown in FIG. 10B. In other embodiments, the reference marker devices may be conventional (i.e., non-minimally invasive) marker devices. In block 1101 of method 1100, patient images may be obtained using an imaging device, such as the imaging device 103 shown in FIGS. 1 and 2. The patent images may be a three-dimensional image dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). In embodiments, the three-dimensional image dataset may be obtained by performing an imaging scan, such as a CT image scan. The three-dimensional image dataset may be a representation of a volume of the patient's internal anatomy, where the anatomical volume may have at least one dimension that is greater than 6 inches (e.g., 6-12 inches) and preferably greater than about 12 inches (e.g., 12-36 inches). In embodiments, the at least one dimension may be an axial dimension along the direction of an imaging scan (e.g., an x-ray CT image scan). The three-dimensional image dataset may be obtained by performing a scan of the patient (i.e., moving an imaging gantry relative to the patient along the length of the patient) while obtaining imaging data. The scan may include the anatomic features to which each of the reference marker devices 1001, 1003 are attached.

In block 1103, at least a first portion of the patient images may be registered to a first patient coordinate system that is based on a first reference marker device 1001 fixed to a first location 1002 on the patient 200. For example, at least a portion of the patient images (e.g., three-dimensional image dataset) may be registered to a first patient coordinate system (i.e., $P_1$ in FIG. 10) based on the first reference marker device 1001 using a patient registration method such as described above with reference to FIG. 3. In embodiments, the entire patient image dataset may be registered to the first patient coordinate system. $P_1$. Alternately, only a portion of the patient image dataset may be registered to the first patient coordinate system. For example, for a three-dimensional volume reconstruction image dataset, a sub-set of the volume that is proximate to the first location 1002 on the patient 200 in the axial direction may be registered to the first patient coordinate system.

In block 1105, at least a second portion of the patient images may be registered to a second patient coordinate system that is based on a second reference marker device 1003 fixed to a second location 1004 on the patient 200. For example, at least a portion of the patient images (e.g., three-dimensional image dataset) may be registered to a second patient coordinate system (i.e., $P_2$ in FIG. 10) based on the second reference marker device 1003 using a patient registration method such as described above with reference to FIG. 3. In embodiments, the entire patient image dataset may be registered to the second patient coordinate system, $P_2$. Alternately, only a portion of the patient image dataset may be registered to the second patient coordinate system. For example, for a three-dimensional volume reconstruction image dataset, a sub-set of the volume that is proximate to the second location 1004 on the patient 200 in the axial direction may be registered to the second patient coordinate system.

In block 1107, the image-guided surgery system 400 may select between display of patient images registered to the first patient coordinate system and display of patient images registered to the second patient coordinate system in the image guided surgery system 400 based on proximity to the first location 1002 and the second location 1004 on the patient 200. In particular, the image-guided surgery system 400 may display patient images that are registered to the first patient coordinate system when the system navigates in a portion of the patient's anatomy that is in closer proximity to the first location 1002 than to the second location 1004 on the patient 200, and the image guided surgery system 400 may display patient images that are registered to the second patient coordinate system when the system navigates in a portion of the patient's anatomy that is in closer proximity to the second location 1004 than to the first location 1002 on the patient 200.

The image-guided surgery system 400 may display the patient images registered to the first patient coordinate system with an overlay or superimposition of graphical element(s) showing the position and/or orientation of one or more objects (e.g., tool(s), instrument(s), an end effector of a robotic arm) that are tracked by a motion tracking system 105. The position and/or orientation of the one or more objects may be shown within the first patient coordinate system, which may be based on the current position and/or orientation of the first reference marker device 1001 tracked by the motion tracking system 105.

The image-guided surgery system 400 may display the patient images registered to the second patient coordinate system with an overlay or superimposition of graphical element(s) showing the position and/or orientation of the one or more objects (e.g., tool(s), instrument(s), an end effector of a robotic arm) that are tracked by the motion tracking system 105. The position and/or orientation of the one or more objects may be shown within the second patient coordinate system, which may be based on the current position and/or orientation of the second reference marker device 1003 tracked by the motion tracking system 105.

In embodiments, the image-guided surgery system 400 may select between display of patient images and motion tracking data in the first and second patient coordinate systems in response to a detected user action. For example, a user may use a pointer device 1050 (see FIG. 10) to touch the first reference marker device 1001 or the second reference marker device 1003, which may cause the system 400 to select between the respective first and second patient coordinate systems. The touching of a reference marker device 1001, 1003 by a pointer device may be detected by the motion tracking system 105. Alternately, the system 400 may select between the first and second patient coordinate systems in response to the pointer device being moved over or touched against a portion of the patient that is closer to one reference marker device than to the other reference marker device. In addition, as discussed above with reference to FIGS. 6A-6C and 7A-7C, in some embodiments the image guided surgery system 400 may display patient images based on the position of a robotic end effector 102 and/or a handheld display device 401. In embodiments, the patient images and motion tracking data may be displayed in either the first patient coordinate system or the second patient coordinate system based on the relative proximity of the robotic end effector 102 and/or handheld display device 401 to either the first reference marker device 1001 or the second reference marker device 1003. In further embodiments, the image-guided surgery system 400 may select between display of patient images and motion tracking data in the first and second patient coordinate systems in response to a user input at a user input device.

Embodiments of the method 1100 may provide improved accuracy and speed of image guided surgery by selectively displaying patient images and motion tracking data (e.g., graphical depictions of tool/instrument pose(s)) in a patient reference frame that is closest to the location of the surgical intervention, and therefore may more accurately represent the patient's actual situation at the time of the intervention. Multiple image-guided surgical interventions may be performed in different areas of the patient using the same patient image dataset registered to different patient reference frames, without having to perform separate image scans and/or placement of the patient reference marker between each intervention, which may improve workflow and greatly reduce time in surgery.

The plurality of patient reference marker devices may also be monitored to detect relative motion of reference marker devices during a surgical procedure. In optional block 1109 of method 1100, a relative motion between the first and second reference marker devices 1001, 1003 may be detected by the motion tracking system 105. The detected relative motion may indicate that a marker device 1001, 1003 is loose and/or has accidentally been bumped causing it to change its position relative to the patient during a surgical procedure. The detected relative motion could also indicate that the portion 1002 of the patient's anatomy to which the first reference marker device 1001 is attached has moved relative to the portion 1004 of the patient's anatomy to which the second reference marker device 1003 is attached. For example, the relative positions of one or more of the vertebrae between positions 1002 and 1004 may have shifted during a surgical procedure. In either case, the relative movement of the marker devices 1001, 1003 may be of sufficient magnitude such that one or both of the patient registrations may no longer accurately represent the current patient situation. In optional block 1111, the user may be notified (e.g., via an audible and/or visual alert) when the detected relative motion between markers 1001 and 1003 exceeds a threshold value. In some embodiments, the threshold value may be between about 1 and 2 mm. The threshold value may be an adjustable parameter, and in embodiments may be a function of a distance of the intended surgical site from one or both markers 1001 and 1003. In some embodiments, the threshold value may be zero, such that any relative motion between the markers 1001 and 1003 detected by the motion tracking system 105 may trigger a notification to the user.

In response to a notification that the detected relative motion between markers 1001 and 1003 exceeds a threshold value, the user may perform an updated imaging scan and register the updated patient images registered to the first and second patient coordinate systems as discussed above. Alternately, the user may elect to continue the procedure with the patient images registered to one or both patient coordinate systems.

In some embodiments, the image guided surgery system 400 may determine that a detected relative motion between reference marker devices 1001, 1003 is the result of one reference marker device 1001, 1003 having moved with respect to the patient. For example, one of the reference marker devices 1001, 1003 may be accidentally bumped or may become loose causing it to move with respect to the location 1002, 1004 on the patient 200 to which it was attached. The determination that a reference marker device 1001, 1003 has moved may be based on a particular reference marker device 1001, 1003 moving by threshold distance and/or in a particular direction while at least one other reference marker device 1001, 1003 has not moved relative to the camera position of the motion tracking system 105. This may indicate that the particular reference marker device has moved with respect to the patient, as opposed to a relative movement of the portions 1002, 1004 of the patient's anatomy to which the reference marker devices 1001, 1003 are attached. In some embodiments, the system 400 may provide a notification to the user that one of the reference markers 1001, 1003 has moved. The user may verify that a particular reference marker device 1001, 1003 has moved using the marker devices 1001, 1003 as fiducials, as discussed above. For example, the user may use a pointer 1050 to touch or trace the marker devices 1001, 1003 and/or position the pointer 1050 along the trajectories of the marker device 1001, 1003 to verify whether a reference marker 1003, 1005 has moved, where a discrepancy between the location of the marker device 1001, 1003 measured using the pointer 1050 and the location of the marker device 1001, 1003 visible in the patient image(s) may indicate that a particular marker device 1001, 1003 has moved.

In some embodiments, the user may perform a registration correction when one of the reference marker devices 1001, 1003 has moved with respect to the patient. The registration correction may be performed without needing to re-scan the patient using the imaging device 103. For example, the user may confirm whether the marker device 1001 that has moved with respect to the patient is still rigidly attached to the patient, and may re-attach the marker device 1001 if necessary. The transformation of the coordinate system of the marker 1001 that has moved may then be adjusted so that it returns to being accurate. This adjustment may be based on the detected motion, including any rotational motion, of the reference marker device 1001 that moved with respect to one or more reference marker devices 1003 that are determined not to have moved with respect to the patient.

Figure 11B:
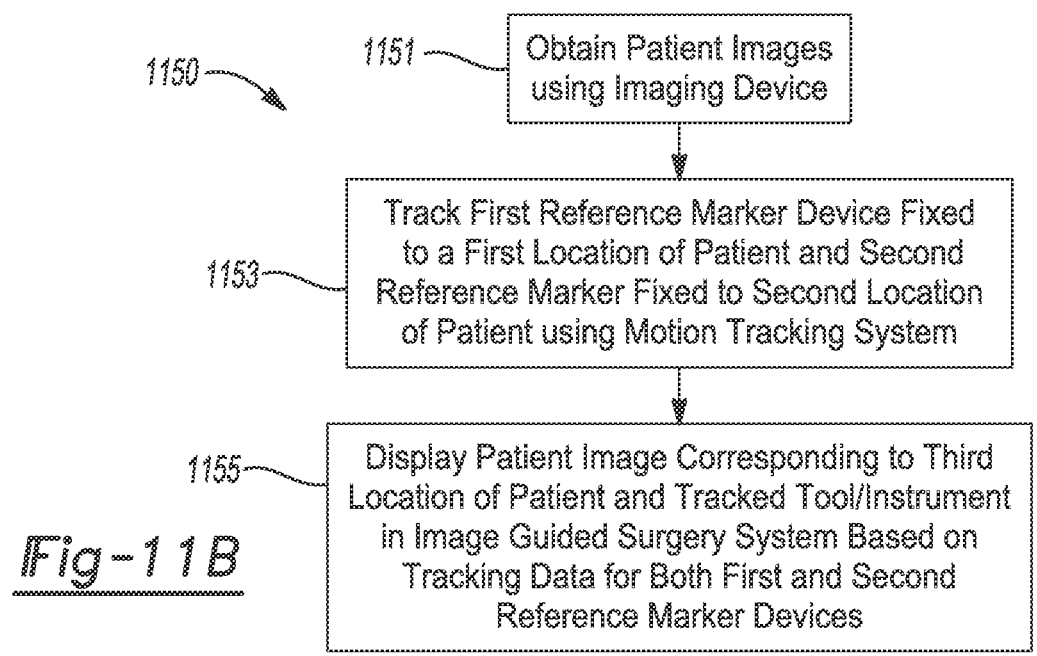
FIG. 11B is a process flow diagram illustrating a further embodiment method of performing image-guided surgery using multiple reference marker devices fixed to a patient.

FIG. 11B is a process flow diagram illustrating a further embodiment method 1150 for performing image-guided surgery using multiple reference marker devices 1001, 1003 fixed to a patient and a blended or interpolated registration of patient images. As noted above, the patient image data set (e.g., volume data set) may depict a volume of the patient's anatomy that does not remain rigid during a surgical procedure. Thus, the tracked position of a tool or instrument in a patient coordinate system based on either reference marker device 1001, 1003 may lose accuracy if the patient's anatomy bends, shifts or otherwise deforms during surgery. Various embodiments may improve the accuracy of the image-guided surgery system by displaying patient images and tracked tools/instruments within a blended or interpolated patient reference coordinate system that is based on multiple patient reference maker devices fixed to different locations on a patient.

Block 1151 of method 1150 may correspond to block 1101 of method 1100, and may include obtaining patient images using an imaging device, such as imaging device 103. In block 1153, a motion tracking system 105 may track a first reference marker device 1001 fixed to a first location 1002 on the patient and a second reference marker device 1003 fixed to a second location 1004 on the patient. In the example of a spinal surgery, for instance, the first reference marker device 1001 may be fixed to a first location 1002 on a first vertebral level of the patient's spine, and the second reference marker device 1003 may be fixed to a second location 1004 on a second vertebral level of the patient's spine.

In block 1155, the image-guided surgery system 400 may display one or more patient images corresponding to a third location of the patient in a blended or interpolated patient reference coordinate system based on tracking data for both the first reference marker device 1001 and the second reference marker device 1003. The patient images may be displayed with an overlay or superimposition of graphical elements) showing the position and/or orientation of the one or more objects (e.g., tool(s), instrument(s), an end effector of a robotic arm) that are tracked by the motion tracking system 105, where the one or more objects may be shown within the blended or interpolated patient coordinate system. The third location of the patient may be, for example, an intervening vertebral level between the vertebral levels to which the first and second reference marker devices 1001, 1003 are attached. The patient image(s) corresponding to the third location may include one or more axial slices of the intervening vertebral level from a three-dimensional dataset (e.g., a 3D CT reconstruction).

In embodiments, the patient image(s) and instrument/tool pose(s) may be displayed in a blended or interpolated reference coordinate system that may be weighted by distance from the first and second reference marker devices 1001, 1003. Other interpolation (i.e., weighting) techniques may be utilized. In some embodiments, the blended or interpolated reference coordinate system may be may be based, at least in part, on a mathematical and/or physical modeling of the anatomical feature of interest. In one example, the patient's spine may be modeled using a cubic spline interpolation, where a set of control points for the spline may be defined with reference to the vertebral levels of interest in the scan data. At least two of the control points of the spline may be defined with reference to the first and second reference marker devices 1001, 1003, which may be fixed to different vertebral levels of the patient's spine. This may enable these control points to be tracked by the motion tracking system 105 during surgery. A fitting algorithm may be used to estimate a change in position and/or orientation of an intervening vertebral level during surgery based on a detected change in the relative positions of the control points tracked using the motion tracking system 105. Such an estimate may be used by the image-guided surgery system 400 to generate a correction factor for the display of patient image(s) and tool/instrument pose(s) in a blended or interpolated patient reference coordinate system. In further embodiments, the physical structure of the anatomy of interest may be modeled based on an analysis of the image data. For example, in the case of a spine procedure, the structure of the patient's spine, including the physical relationship of each of the vertebral levels of interest, and optionally the various motions (e.g., bending, torsional movements, compression and/or stretching) of the patient's spine, may be modeled based on an analysis of the patient image data set (e.g., CT data). This modeling may be used in conjunction with the tracked position of each of the patient reference marker devices 1001, 1003 to generate suitable correction(s) for display of patient images and tool poses in a blended or interpolated patient reference coordinate system during a surgical procedure.

Figure 11C:
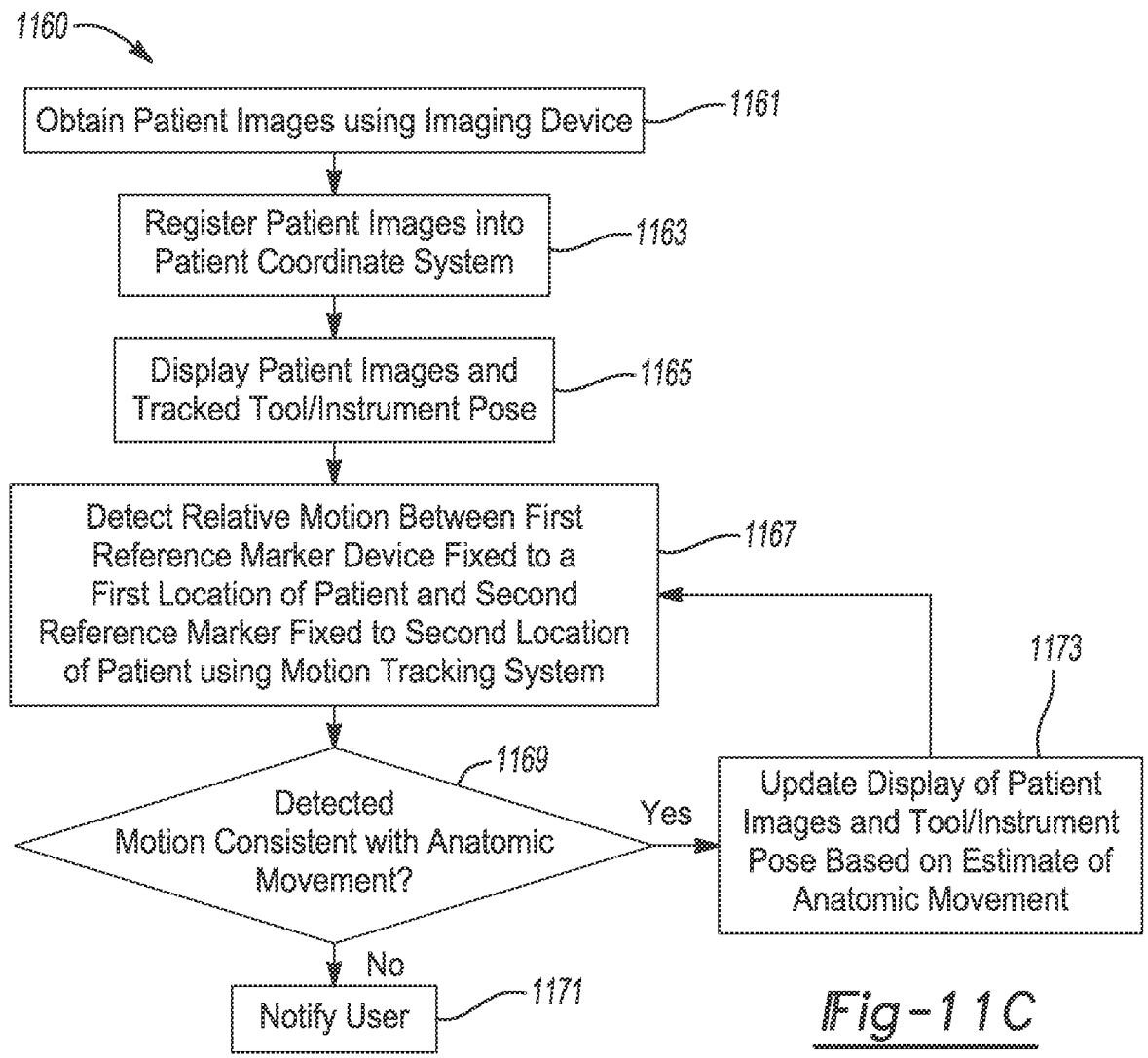
FIG. 11C is a process flow diagram illustrating a further embodiment method of performing image-guided surgery using multiple reference marker devices fixed to a patient FIG. 12 schematically illustrate a computing device which may be used for performing various embodiments.

FIG. 11C illustrates a further embodiment method 1160 for performing image-guided surgery using multiple reference marker devices 1001, 1003 fixed to a patient. Block 1161 of method 1160 may correspond to block 1101 of method 1100, and may include obtaining patient images using an imaging device, such as imaging device 103. In block 1163, the patient images may be registered to a patient coordinate system using a patient registration method, such as described with reference to FIG. 3. In some embodiments, the patient images may be registered to multiple patient coordinate systems based on respective first and second reference marker devices 1001 and 1003, such as described above with reference to FIG. 11A. In block 1165, patient image(s) and tool/instrument pose(s) may be displayed in a patient reference coordinate system. The patient reference coordinate system may be based on the tracked position one of the first and second reference marker devices 1001, 1003, as described with reference to FIG. 11A or may be displayed in a blended or interpolated coordinate system based on the tracked positions of both of the reference marker devices 1001, 1003, as described with reference to FIG. 11B.

In block 1167, a motion tracking system 105 may detect a relative motion between the first reference marker device 1001 fixed to a first location 1002 on the patient and a second reference marker device 1003 fixed to a second location 1003 on the patient. As discussed above, a relative motion between reference marker devices 1001, 1003 may be due to a shifting of the patient's anatomy during surgery (e.g., a bending, twisting, compression and/or stretching of the spine in the case of a spine surgery) or may be the result of a movement of a reference marker device 1001, 1003 moving with respect to the patient. Either case may result in a loss in registration accuracy. However, typically a greater loss in registration accuracy will result from a reference marker device moving with respect to its attachment point on the patient, such as by an accidental bumping, than through a natural movement of the patient's anatomy. In determination block 1069, the image guided surgery system 400 may determine whether the detected motion of the reference marker devices 1001, 1003 is consistent with an anatomic movement. In other words, the system 400 may determine whether the detected motion is more likely due to a shift in the anatomy during surgery or due to a movement of a reference marker device 1001, 1003 relative to the patient. The determination may be based on a software model of the anatomical region of interest (e.g., a spine) and/or may be based on a set of pre-determined boundary conditions which may define the possible or likely movements of the anatomy that may occur during the surgical procedure. In one non-limiting example, the system 400 may determine that a particular detected movement of the reference marker devices 1001, 1003 is not consistent with an anatomic movement when the detected motion corresponds to a movement that is not anatomically possible (e.g., would result in too great of a bend radius in the case of a human spine, would result in a superimposition of multiple rigid structures, such as vertebrae, etc.). In response to determining that that the detected motion is not consistent with an anatomic movement (i.e., determination block 1069="No"), the system 400 may notify the user (e.g., via an audible and/or visual alert) in block 1171. The notification may indicate that one of the reference marker devices 1001, 1003 has likely moved and that the registration may no longer be sufficiently accurate.

In response to determining that the detected motion is consistent with an anatomic movement (i.e., determination block 1069="Yes"), the system 400 may update the display of the patient image(s) and tool pose(s) based on an estimation of the anatomic movement corresponding to the detected relative motion of the reference marker devices 1001 and 1003 in block 1173. The estimate may be determined using a mathematic and/or physical model of the anatomic feature of interest (e.g., the vertebral levels of the spine) as described above with reference to FIG. 11B.

Figure 12:
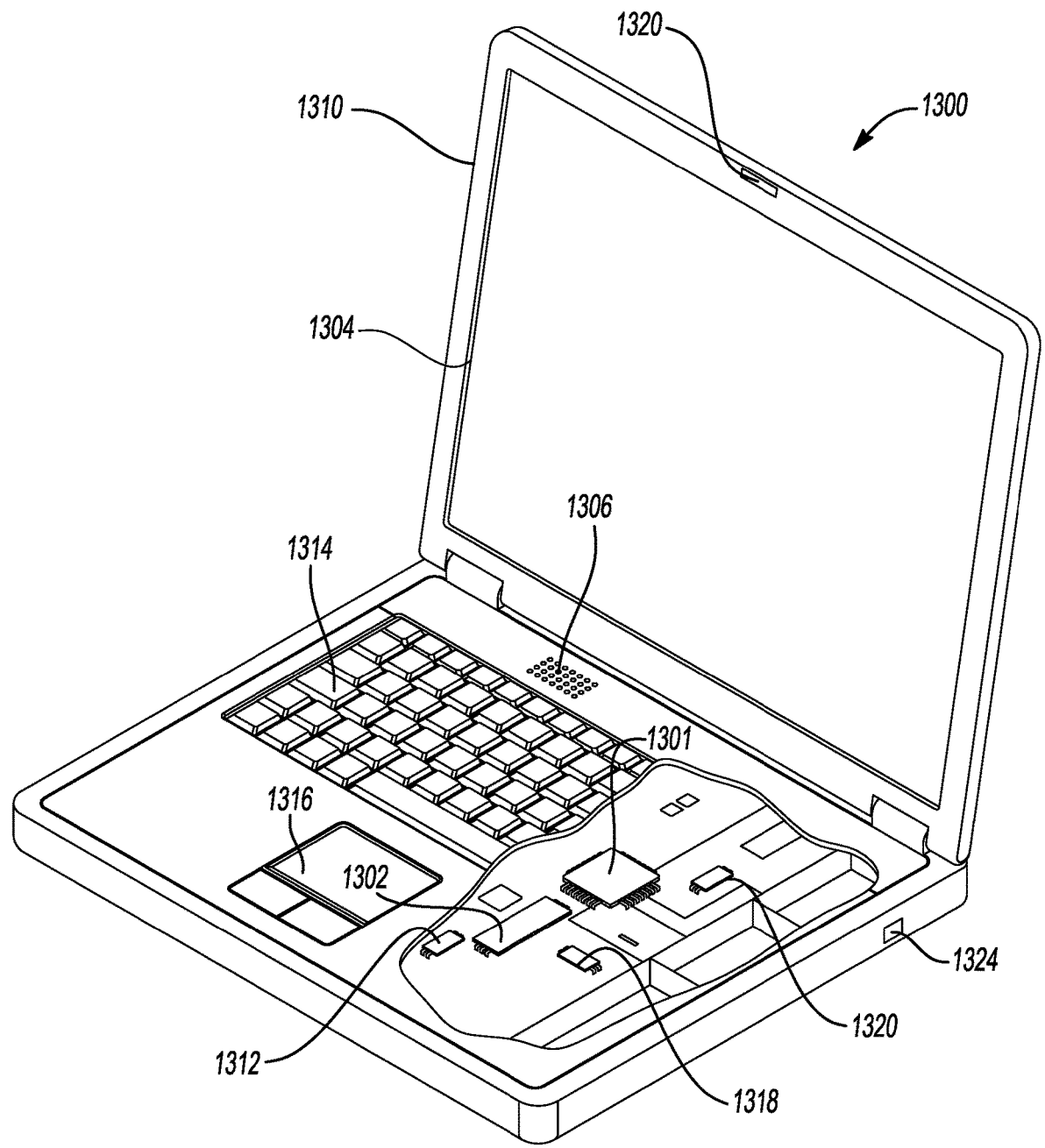

FIG. 12 is a system block diagram of a computing device 1300 useful for performing and implementing the various embodiments described above. The computing device 1300 may perform the functions of an image guided surgery system 400, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. The computing device 1300 may also include a camera 1320 coupled to the processor 1301 for obtaining photographs and/or video images that may optionally be shown on the display 1304. A handheld computing device (e.g., a tablet, smartphone) may include camera 1320 in a rear-facing configuration for display of real-time video images as discussed above in connection with FIGS. 7D and 7E. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

The invention claimed is:

1. A method for performing image-guided surgery using multiple reference marker devices fixed to a patient, the method comprising:
   obtaining image data of a patient using an imaging device;
   associating a first portion of the image data with a first reference marker device fixed to a first location on the patient;
   associating a second portion of the image data with a second reference marker device fixed to a second location on the patient;
   displaying at least a portion of the image data of the patient on a display screen of a movable display device;
   tracking movement of the movable display device with respect to at least one of the first reference marker device fixed to the first location on the patient and the second reference marker device fixed to the second location on the patient; and
   modifying the image data displayed on the display screen of the movable display device in response to relative movement occurring between the movable display device and one or more of the first reference marker device fixed to the first location on the patient and the second reference marker device fixed to the second location on the patient.

2. The method of claim 1, wherein modifying the image data includes selecting between display of one or more first patient images of the first portion of the image data and one or more second patient images of the second portion of the image data based on a proximity of the movable display device to the first and second locations.

3. The method of claim 1, further comprising:
detecting a relative movement between the first and second reference marker devices; and
notifying a user when the relative movement is greater than a threshold value.

4. The method of claim 1, further comprising determining whether a reference marker device has moved relative to the patient.

5. The method of claim 4, wherein the first reference marker device and the second reference marker device are visible in the image data.

6. The method of claim 4, further comprising performing a registration correction in response to determining that a reference marker device has moved relative to the patient.

7. The method of claim 6, wherein the registration correction is performed without re-scanning the patient to obtain additional patient images.

8. The method of claim 1, wherein the image data comprises a portion of a three-dimensional dataset of anatomy of the patient; and
further comprising displaying a second image of the patient obtained by a camera on the movable display device on the display screen, wherein the portion of a three-dimensional dataset of anatomy of the patient is displayed overlaying the second image.

9. The method of claim 8, wherein the second image comprises a real-time video image of the patient.

10. The method of claim 8, wherein the portion of the three-dimensional dataset comprises a three-dimensional volume rendering of a portion anatomy of the patient visible in the second image.

11. The method of claim 10, further comprising:
performing a calibration process to match the three-dimensional volume rendering to a view of the patient in the second image; and
updating the three-dimensional volume rendering based on movement of the camera relative to the patient.

12. The method of claim 11, further comprising adjusting a transparency of the three-dimensional volume rendering relative to the second image on the movable display device in response to a user input.

13. The method of claim 8, wherein the three-dimensional dataset comprises at least one of an x-ray computed tomography (CT) reconstruction and a magnetic resonance (MR) image data.

14. The method of claim 13, wherein displaying image data on the display screen of the movable display device comprises:
determining at least one of a first position and a first orientation of the movable display device with respect to one of the first and second reference marker devices; and
displaying a first portion of the three-dimensional dataset of anatomy of the patient on the display screen based on the determined a least one of the first position and the first orientation of the movable display device.

15. The method of claim 14, wherein displaying the first portion of the three-dimensional dataset comprises displaying at least one two-dimensional slice of the three-dimensional dataset of anatomy of the patient in at least one first plane defined by the first position and/or the first orientation of the movable display device with respect to the patient; and
wherein modifying at least a portion of the image data displayed on the display screen comprises displaying the at least one two-dimensional slice of the three-dimensional dataset of anatomy of the patient in at least one second plane defined by a detected second position and/or orientation of the movable display device with respect to the patient.

16. The method of claim 15, wherein the at least one two-dimensional slice comprises at least one of an axial, sagittal and coronal slice of anatomy of the patient; and
wherein the at least one two-dimensional slice comprises a coronal slice in a plane offset from the movable display device by a predetermined distance.

17. The method of claim 14, wherein displaying the first portion of the three-dimensional dataset comprises displaying a three-dimensional rendering of anatomy of the patient in a first view based on the first position and/or the first orientation of the movable display device with respect to the patient; and
wherein modifying at least a portion of the image data displayed on the display screen comprises displaying the three-dimensional rendering of anatomy of the patient in a second view based on a detected second position and/or orientation of the movable display device with respect to the patient.

18. The method of claim 1, wherein the movable display device is further defined as a handheld display device; and
further comprising positioning the handheld display device closer to the first reference marker device than to the second reference marker device.

19. The method of claim 18, wherein the handheld display device comprises at least one of a tablet computer, a smartphone, and a pendant controller.

20. The method of claim 1, further comprising displaying the image data of the patient on a second display screen.

* * * * *